United States Patent [19]

Fujioka et al.

[11] Patent Number: 5,591,751
[45] Date of Patent: Jan. 7, 1997

[54] PERIPHERAL VASODILATORS

[75] Inventors: Takafumi Fujioka; Shuji Teramoto; Michinori Tanaka; Hiroshi Shimizu; Fujio Tabusa; Michiaki Tominaga, all of Tokushima, Japan

[73] Assignee: Otsuka Pharmaceutical Co., Ltd., Tokyo, Japan

[21] Appl. No.: 318,801

[22] PCT Filed: Feb. 3, 1994

[86] PCT No.: PCT/JP94/00157

§ 371 Date: Oct. 14, 1994

§ 102(e) Date: Oct. 14, 1994

[87] PCT Pub. No.: WO94/19339

PCT Pub. Date: Sep. 1, 1994

[30] Foreign Application Priority Data

Feb. 16, 1993 [JP] Japan ..................... 5-026594

[51] Int. Cl.$^6$ ............. A61K 31/47; C07D 215/227; C07D 215/48
[52] U.S. Cl. ................. 514/312; 546/156
[58] Field of Search ............. 546/156; 514/312

[56] References Cited

U.S. PATENT DOCUMENTS

| | | | |
|---|---|---|---|
| 4,454,130 | 6/1984 | Tominaga | 514/235.2 |
| 4,468,402 | 8/1984 | Tominaga | 514/312 |
| 4,487,772 | 12/1984 | Tominaga | 514/252 |
| 5,306,719 | 4/1994 | Tamada | 514/253 |

FOREIGN PATENT DOCUMENTS

| | | |
|---|---|---|
| 0202760A2 | 11/1986 | European Pat. Off. . |
| 0255134 | 2/1988 | European Pat. Off. . |
| 0382185 | 8/1990 | European Pat. Off. . |
| 51-68574 | 6/1976 | Japan . |
| 51-65770 | 6/1976 | Japan . |
| 52-283 | 1/1977 | Japan . |
| 52-282 | 1/1977 | Japan . |
| 52-83380 | 7/1977 | Japan . |
| 51-118771 | 10/1977 | Japan . |
| 52-118474 | 10/1977 | Japan . |
| 54-16478 | 2/1979 | Japan . |
| 57-154129 | 9/1982 | Japan . |
| 57-171974 | 10/1982 | Japan . |
| 59-29668 | 2/1984 | Japan . |
| 63-35562 | 2/1988 | Japan . |
| JP94/00157 | 1/1994 | WIPO . |
| WO94/19339 | 9/1994 | WIPO . |

OTHER PUBLICATIONS

Copy of International Search Report dated Jun. 15, 1994 for International Application No. PCT/JP94/00157.

Primary Examiner—C. Warren Ivy
Assistant Examiner—D. Margaret M. Mach
Attorney, Agent, or Firm—Finnegan, Henderson, Farabow, Garrett & Dunner

[57] ABSTRACT

Peripheral vasodilating agents containing, as the active ingredient, carbostyril derivatives represented by the general formula:

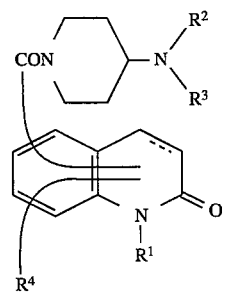

or a salt thereof; and novel carbostyril derivatives included within the scope of the above-mentioned general formula.

31 Claims, No Drawings

PERIPHERAL VASODILATORS

BACKGROUND OF THE INVENTION

The present invention relates to peripheral vasodilators each comprising a carbostyril derivative as an active ingredient, as well as to novel carbostyril derivatives having an excellent peripheral vasodilating activity.

There have been made a number of studies on various carbostyril derivatives and their pharmacological activities. For example, Japanese Patent Application Kokai (Laid-Open) No. 3182/1989 describe that the carbostyril derivatives represented by the following general formula:

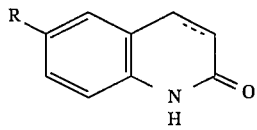

[wherein, R is a group of the formula:

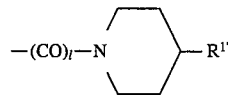

or a group of the formula:

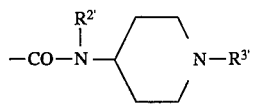

($R^{1'}$ is a group of the formula: —$NR^{4'}R^{5'}$ or the like; $R^{2'}$ is a hydrogen atom or a lower alkyl group; and $R^{3'}$ is a hydrogen atom, a lower alkyl group or the like)] have a myocardial contraction increasing activity, a coronary blood flow increasing activity, a hypotensive activity, a norepinephrin vasocontraction inhibitory effect and an anti-inflammatory effect and are useful as a cardiotonic for treating various heart diseases, an anti-hypertensive agent and an anti-inflammatory agent. It is not known, however, that such carbostyril derivatives have a peripheral vasodilating activity.

In addition to the above, various carbostyril derivatives, each of which having chemical structural formula similar to that of the carbostyril derivative represented by the below-mentioned general formula (1), have been known in some prior art references, for example Japanese Patent Kokai (Laid-open) No. Sho 57-171974 (1982) [Japanese Patent Publication No. Sho 64-9313 (1989)]; Japanese Patent Kokai (Laid-open) No. Sho 57-154129 (1982) [Japanese Patent Publication No. Sho 64-53248 (1989)]; Japanese Patent Kokai (Laid-open) No. Sho 59-29668 (1984) [Japanese Patent Publication No. Hei 2-22751 (1990)]; Japanese Patent Kokai (Laid-open) Nos. Sho 54-16478 (1979); Sho 55-85520 (1980); Sho 51-65770 (1976); Sho 51-68574 (1976); Sho 51-118771 (1976); Sho 52-282 (1977); Sho 52-283 (1977); Sho 51-118474 (1977); Sho 52-83380 (1977); Sho 63-35562 (1988) as well as U.S. Pat. Nos. 4,487,772; 4,454,130; 4,468,402; 4,886,809; 5,071,856 (EP-A-0255134); U.S. Pat. No. 4,845,100 (EP-A-0202760); U.S. Pat. Nos. 4,514,401; 4,455,422; 4,567,187; 4,460,593; 4,619,932 and 5,008,274 (EP-A-0240015).

The carbostyril derivatives disclosed in the above-mentioned prior art references indeed possess certain pharmacological activities, for example myocardial contraction increasing activity (positive inotropic activity), coronary blood flow increasing activity, hypotensive activity and antiinflammatory activity, etc. However, such known carbostyril derivatives do not possess any peripheral vasodilating activities at all.

Hence, development of novel carbostyril derivatives having a peripheral vasodilating activity has been desired.

SUMMARY OF THE INVENTION

The present inventors synthesized a number of carbostyril derivatives and examined their pharmacological activities. As a result, the present inventors found that each of the carbostyril derivatives represented by the following general formula (1) and their salts

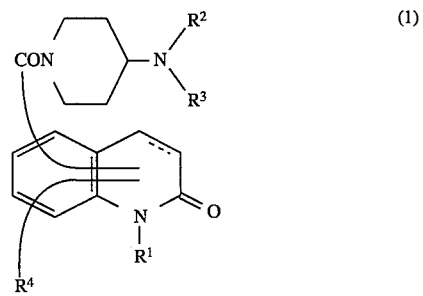

(wherein, $R^1$ represents a hydrogen atom or a lower alkyl group; $R^2$ and $R^3$, which may be the same or different, each represent a hydrogen atom, a lower alkyl group, a phenylthio-lower alkyl group, a phenoxy-lower alkyl group which may have, on the phenyl ring, 1–3 substituents selected from the group consisting of halogen atoms and lower alkoxy groups, or a phenyl-lower alkyl group; $R^4$ represents a hydrogen atom, a lower alkyl group, a lower alkoxy group, a nitro group, an amino group or a phenyl-lower alkylamino group; and the carbon-carbon bond between 3- and 4-positions in the carbostyril skeleton represents a single bond or a double bond) have peripheral vasodilating activity and are useful as peripheral vasodilators.

The present inventors further found that, among the carbostyril derivatives represented by the above general formula (1) and their salts, the carbostyril derivatives represented by the following general formula (1A) and their salts

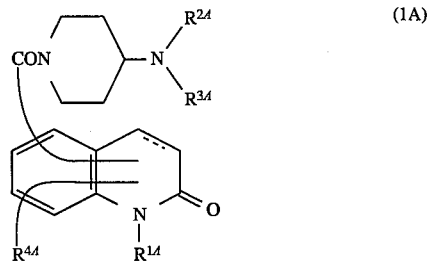

(wherein, $R^{1A}$ represents a hydrogen atom or a lower alkyl group; $R^{2A}$ and $R^{3A}$, which may be the same or different, each represent a hydrogen atom, a lower alkyl group, a phenylthio-lower alkyl group, a phenoxy-lower alkyl group having, on the phenyl ring, 1–3 substituents selected from the group consisting of halogen atoms and lower alkoxy groups, or a phenyl-lower alkyl group; $R^{4A}$ represents a hydrogen atom, a lower alkyl group, a lower alkoxy group, a nitro group, an amino group or a phenyl-lower alkylamino group; the carbon-carbon bond between 3- and 4-positions in the carbostyril skeleton represents a single bond or a double bond; provided that when both $R^{1A}$ and $R^{4A}$ are a hydrogen atom and the substituent of the formula:

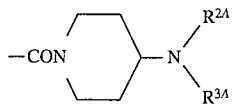

bonds to the 6-position of the carbostyril skeleton and one of $R^{2A}$ and $R^{3A}$ is a hydrogen atom, a lower alkyl group or a phenyl-lower alkyl group, then the other of $R^{2A}$ and $R^{3A}$ should not be a hydrogen atom, a lower alkyl group or a phenyl-lower alkyl group; are novel substances and are useful as a peripheral vasodilator.

DETAILED DESCRIPTION OF THE INVENTION

That is, the present inventors found that each of the carbostyril derivatives of general formula (1) and general formula (1A) [these two general formulas are hereinafter referred to simply as general formula (1)] and their salts has an excellent peripheral vasodilating activity, is useful as an agent for improving peripheral circulatory disturbances caused by arterial diseases (e.g. Berger disease, obstructive arteriosclerosis, Raynaud disease and Raynaud syndrome), venous diseases (e.g. venous thrombosis and thrombophlebites) and other diseases (e.g. congelation, frostbite, feeling of cold and decubitus), and is effective for the preventions and treatments of feeling of coldness being accompanied by oversensitity to the cold and hypnagogic disturbance, etc.

The carbostyril derivatives of general formula (1) and their salts according to the present invention are characterized particularly in that while they have an excellent peripheral vasodilating activity, they show low pharmacological side-effects to the heart, i.e. a low effect to heart rate, a low hypotensive effect and a low myocardial contraction effect.

Specific examples of the individual groups mentioned with respect to general formula (1) are as follows.

"Lower alkyl group" can be exemplified by $C_{1-6}$ straight- or branched-chain alkyl groups such as methyl, ethyl, propyl, isopropyl, butyl, tert-butyl, pentyl and hexyl groups and the like.

"Phenylthio-lower alkyl group" can be exemplified by phenylthioalkyl groups in which the alkyl moiety is a $C_{1-6}$ straight- or branched-chain alkyl group, such as phenylthiomethyl, 2-phenylthioethyl, 1-phenylthioethyl, 3-phenylthiopropyl, 4-phenylthiobutyl, 1,1-dimethyl-2-phenylthioethyl, 5-phenylthiopentyl, 6-phenylthiohexyl and 2-methyl-3-phenylthiopropyl groups and the like.

"Lower alkoxy group" can be exemplified by $C_{1-6}$ straight- or branched-chain alkoxy groups such as methoxy, ethoxy, propoxy, isopropoxy, butoxy, tert-butoxy, pentyloxy and hexyloxy groups and the like.

"Phenyl-lower alkyl group" can be exemplified by phenylalkyl groups in which the alkyl moiety is a $C_{1-6}$ straight- or branched-chain alkyl group, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl and 2-methyl-3-phenylpropyl groups and the like.

"Phenyl-lower alkylamino group" can be exemplified by phenylalkylamino groups in which the alkyl moiety is a $C_{1-6}$ straight- or branched-chain alkyl group, such as benzylamino, (2-phenylethyl)amino, (1-phenylethyl)amino, (3-phenyl-propyl)amino, (4-phenylbutyl)amino, (1,1-dimethyl-2-phenylethyl)amino, (5-phenylpentyl)amino, (6-phenylhexyl)amino and (2-methyl-3-phenylpropyl)amino group and the like.

"Halogen atom" can be exemplified by a fluorine atom, a chlorine atom, a bromine atom, an iodine atom and the like.

The substituent of the formula:

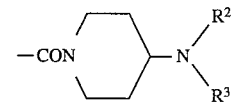

and $R^4$ respectively bond each to any one of 3- to 8-positions in the carbostyril skeleton.

"Phenoxy-lower alkyl group having, on the phenyl ring, 1–3 substituents selected from the group consisting of halogen atoms and lower alkoxy groups" can be exemplified by phenoxyalkyl groups which each have, on the phenyl ring, 1–3 substituents selected from halogen atoms and $C_{1-6}$ straight- or branched-chain alkoxy groups in which the lower alkyl moiety is a $C_{1-6}$ straight- or branched-chain alkyl group, such as (2-chlorophenoxy)methyl, 1-(3-chlorophenoxy)ethyl, 2-(4-chlorophenoxy)ethyl, 3-(4-fluorophenoxy)propyl, 4-(3-bromophenoxy)butyl, 1,1-dimethyl-2-(4-iodophenoxy)ethyl, 5-(2,6-dichlorophenoxy)pentyl, 6-(3,4-dichlorophenoxy)hexyl, 2-methyl-3-(2,4-dibromophenoxy)propyl, 3-(2,4,6-trichlorophenoxy)propyl, (4-methoxyphenoxy)methyl, 2-(3-methoxyphenoxy)ethyl, 3-(ethoxyphenoxy)ethyl, 1-(2-propoxyphenoxy)ethyl, 3-(4-n-butoxyphenoxy)propyl, 4-(3-pentyloxyphenoxy)butyl, 1,1-dimethyl-2-(2-hexyloxyphenoxy)ethyl, 2-(3,4-dimethoxyphenoxy)ethyl, 5-(2,6-dimethoxyphenoxy)pentyl and 6-(2,4,6-trimethoxyphenoxy)hexyl groups and the like.

"Phenoxy-lower alkyl group which may have, on the phenyl ring, 1–3 substituents selected from the group consisting of halogen atoms and lower alkoxy groups" can be exemplified not only by the above-mentioned phenoxy-lower alkyl groups each having, on the phenyl ring, 1–3 substituents selected from the group consisting of halogen atoms and lower alkoxy groups but also by phenoxyalkyl groups which may each have, on the phenyl ring, 1–3 substituents selected from the group consisting of $C_{1-6}$ straight- or branched-chain alkoxy groups and halogen atoms in which the lower alkyl moiety is a $C_{1-6}$ straight- or branched-chain alkyl group, such as phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl and 2-methyl-3-phenoxypropyl groups and the like.

The compounds represented by the general formula (1) according to the present invention can be produced by various processes. Shown below are preferable processes.

[Reaction formula-1]

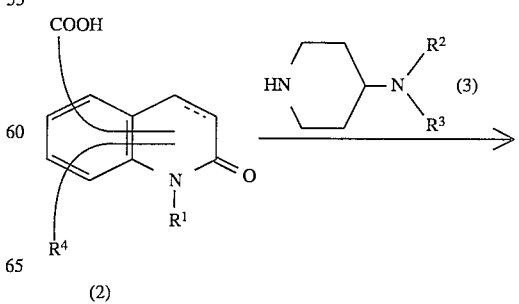

[Reaction formula-1] -continued

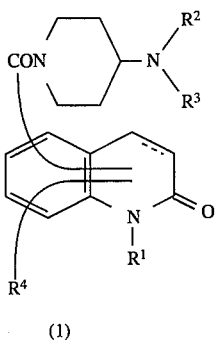

(1)

(wherein, R¹, R2, R³, R⁴ and the carbon-carbon bond between 3- and 4-positions in the carbostyril skeleton are the same as defined above).

The process shown by the above Reaction formula-1 is carried out by reacting a carbostyril derivative represented by general formula (2) or a compound obtained by activating the carboxyl group of said derivative, with an amine represented by general formula (3) or a compound obtained by activating the amino group of said amine, according to an ordinary amido-bond formation reaction. In the reaction, the known conditions used in amido-bond formation reaction can be employed easily. The process includes, for example, (a) a mixed acid anhydride process which comprises reacting a carbostyril derivative (2) with an alkylhalocarboxylic acid to form a mixed acid anhydride and reacting the anhydride with an amine (3); (b) an active ester process which comprises converting a carbostyril derivative (2) into an active ester such as p-nitrophenyl ester, N-hydroxysuccinimide ester, 1-hydroxybenzotriazole ester or the like and reacting the active ester with an amine (3); (c) a carbodiimide process which comprises subjecting a carbostyril derivative (2) and an amine (3) to a condensation reaction in the presence of an activating agent such as dicyclohexylcarbodiimide, carbonyldiimidazole or the like; and (d) other processes. The other processes (d) include, for example, a process which comprises converting a carbostyril derivative (2) into a carboxylic acid anhydride using a dehydrating agent such as acetic anhydride or the like and reacting the carboxylic acid anhydride with an amine (3); a process which comprises reacting an ester of a carbostyril derivative (2) and a lower alcohol with an amine (3) at a high pressure at a high temperature; and a process which comprises reacting an acid halide of a carbostyril derivative (2), i.e. a carboxylic acid halide with an amine (3). There may be also employed, for example, a process which comprises activating a carbostyril derivative (2) with a phosphorus compound such as triphenylphosphine, diethyl cyanophosphate, diethyl chlorophosphate or the like and reacting the resulting compound with an amine (3).

The mixed acid anhydride used in the mixed acid anhydride process (a) can be obtained by an ordinary Schotten-Baumann reaction. The anhydride is reacted with an amine (3) generally without being isolated, whereby a compound of general formula (1) can be produced. The Schotten-Baumann reaction is conducted in the presence of a basic compound. The basic compound is a compound conventionally used in the Schotten-Baumann reaction and includes, for example, organic bases such as triethylamine, trimethylamine, pyridine, N,N-dimethylaniline, N-methylmorpholine, 4-dimethylaminopyridine, 1,5-diazabicyclo[4.3.0]non-ene-5 (DBN), 1,8-diazabicyclo[5.4.0]undecene-7 (DBU), 1,4-diazabicyclo[2.2.2]octane (DABCO) and the like, and inorganic bases such as potassium carbonate, sodium carbonate, potassium hydrogencarbonate, sodium hydrogencarbonate and the like. The reaction is conducted generally at −20° C. to 100° C., preferably at 0°–50° C., and the reaction time is 5 minutes to 10 hours, preferably 5 minutes to 2 hours. The reaction of the resulting mixed acid anhydride with an amine (3) is conducted generally at −20° C. to 150° C., preferably at 10°–50° C., and the reaction time is 5 minutes to 10 hours, preferably 5 minutes to 5 hours. The mixed acid anhydride process (a) is conducted in an appropriate solvent or in the absence of any solvent. The solvent may be any solvent conventionally used in the mixed acid anhydride process, and can be exemplified by halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as N,N-dimethylformamide, dimethyl sulfoxide, hexamethylphosphoric triamide and the like. The alkylhalocarboxylic acid used in the mixed acid anhydride process (a) includes, for example, methyl chloroformate, methyl bromoformate, ethyl chloroformate, ethyl bromoformate and isobutyl chloroformate. The alkylhalocarboxylic acid is used in an amount of generally at least 1 mole, preferably about 1–2 moles per mole of the carbostyril derivative (2). The amine (3) is used in an amount of generally at least 1 mole, preferably about 1–2 moles per mole of the carbostyril derivative (2).

The active ester process (b), when, for example, N-hydroxysuccinimide ester is used, is conducted in an appropriate solvent which does not adversely affect the reaction. Specific examples of the solvent are halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as N,N-dimethylformamide, dimethyl sulfoxide, hexamethylphosphoric triamide and the like. The reaction is conducted at 0°–150° C., preferably at 10°–100° C. and is complete in 5–30 hours. With respect to the desirable proportions of the amine (3) and the N-hydroxysuccinimide ester, the former is used in an amount of generally at least 1 mole, preferably 1–2 moles per mole of the latter.

The process which comprises reacting a carboxylic acid halide with an amine (3) [this is a process included in the other processes (d)], can be conducted in the presence of a dehydrohalogenating agent in an appropriate solvent. As to the dehydrohalogenating agent, an ordinary basic compound is used. The basic compound can be selected from various known basic compounds and can be exemplified by not only the basic compounds usable in the above Schotten-Baumann reaction but also sodium hydroxide, potassium hydroxide, sodium hydride, potassium hydride, silver carbonate and alcoholates (e.g. sodium methylate and sodium ethylate). Further, an excess amount of amine (3) can also be used as dehydrohalogenating agent. The solvent can be exemplified by the solvents usable in the mixed acid anhydride process (a), alcohols (e.g. methanol, ethanol, propanol, butanol, 3-methoxy-1-butanol, ethyl cellosolve and methyl cellosolve), water, pyridine, acetone, acetonitrile and mixtures thereof. The proportions of the amine (3) and the carboxylic acid halide used are not particularly restricted and can be appropriately selected from a wide range, but the carboxylic acid halide is used in an amount of generally at least about 1 mole, preferably about 1–2 moles per mole of the amine (3). The reaction is conducted generally at about −30° C. to 180° C., preferably at about 0°–150° C. and is complete generally in about 5 minutes to 30 hours.

In the above process, the carboxylic acid halide can be produced, for example, by reacting a carbostyril derivative (2) with a halogenating agent in the presence or absence of a solvent. The solvent may be any solvent which does not adversely affect the reaction, and includes, for example, aromatic hydrocarbons (e.g. benzene, toluene and xylene), halogenated hydrocarbons (e.g. chloroform, methylene chloride and carbon tetrachloride), ethers (e.g. dioxane, tetrahydrofuran and diethyl ether), dimethylformamide, dimethyl sulfoxide and mixtures thereof. The halogenating agent may be an ordinary halogenating agent used for converting the hydroxyl group of carboxyl group into a halogen atom, and can be exemplified by thionyl chloride, phosphorus oxychloride, phosphorus oxybromide, phosphorus pentachloride and phosphorus pentabromide. The proportions of the carbostyril derivative (2) and the halogenating agent used are not particularly restricted and can be appropriately selected. The latter is used generally in large excess of the former when the reaction is conducted in the absence of any solvent, and in an amount of generally at least about 1 mole, preferably 2–4 moles per mole of the former when the reaction is conducted in a solvent. The reaction temperature and reaction time are not particularly restricted, either. However, the reaction temperature is generally about room temperature to 100° C., preferably 50°–100° C. and the reaction time is about 30 minutes to 6 hours.

In the reaction, when the carbon-carbon bond between 3- and 4-positions in the carbostyril skeleton of the compound (2) is a double bond, it occurs in some cases that the 2-position of the carbostyril skeleton of the compound is halogenated as well to form a compound represented by the following general formula (A):

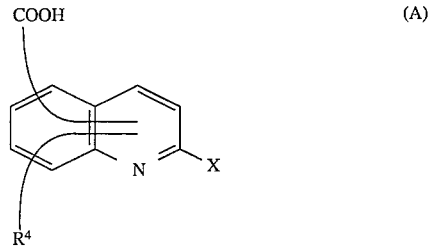

(A)

(wherein, X represents a halogen atom; and $R^4$ is the same as defined above). This compound (A) is reacted with a compound (3) as it is, under the same conditions as mentioned above, to convert into a compound represented by the following general formula (B)

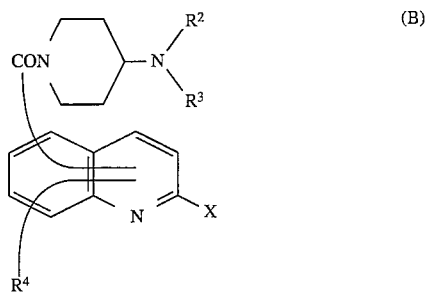

(B)

(wherein, $R^2$, $R^3$, $R^4$ and X are the same as defined above); the compound (B) is hydrolyzed or reacted with a phenyl-lower alcohol such as benzyl alcohol or the like; the resulting compound is reduced; thereby, an intended compound (1) can be obtained.

The hydrolysis of the compound (B) is achieved by heating the compound (B) at 50°–150° C., preferably at 70°–120° C. for about 0.5–24 hours in the presence of, for example, a hydrohalogenic acid (e.g. hydrochloric acid or hydrobromic acid), an inorganic acid (e.g. sulfuric acid or phosphoric acid), an alkali metal hydroxide (e.g. potassium hydroxide or sodium hydroxide), an inorganic alkali compound (e.g. sodium carbonate, potassium carbonate or potassium hydrogencarbonate), or an organic acid (e.g. acetic acid).

The reaction of the compound (B) with the phenyl-lower alcohol is conducted by reacting them in an appropriate solvent in the presence of a basic compound generally at 0°–100° C., preferably at about 0°–70° C. for 1–5 hours. The desirable amount of the phenyl-lower alcohol used is at least 1 mole, preferably 1–2 moles per mole of the compound (B). The solvent and the basic compound can be any solvent and basic compound mentioned with respect to the process which comprises reacting a carboxylic acid halide with an amine (3). The subsequent reduction reaction is conducted under the same conditions as employed in (1) the catalytic reduction of a compound (1e) in Reaction formula 3 to be described later.

The process which comprises activating a carbostyril derivative (2) with a phosphorus compound such as triphenylphosphine, diethyl cyanophosphate, diethyl chlorophosphate, N,N-bis(2-oxo-3-oxazolidinyl)phosphinic acid chloride or the like and reacting the resulting compound with an amine (3), can be conducted in an appropriate solvent. The solvent can be any solvent which does not adversely affect the reaction. Specific examples thereof are halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as N,N-dimethylformamide, dimethyl sulfoxide, hexamethylphosphoric triamide and the like. In the reaction, since the amine (3) acts also as a basic compound, the use of the amine (3) in excess of the stoichiometric amount allows the reaction to proceed favorably. However, it is possible to use, as necessary, other basic compound, for example, an organic base (e.g. triethylamine, trimethylamine, pyridine, N,N-dimethylaniline, N-methylmorpholine, DBN, DBU or DABCO) or an inorganic base (e.g. potassium carbonate, sodium carbonate, potassium hydrogencarbonate or sodium hydrogencarbonate). The reaction is conducted at about 0°–150° C., preferably at about 0°–100° C. and is complete in about 10 minutes to 30 hours. The phosphorus compound and the amine (3) are used each in an amount of generally at least about 1 mole, preferably 1–3 moles per mole of the carbostyril derivative (2).

[Reaction formula-2]

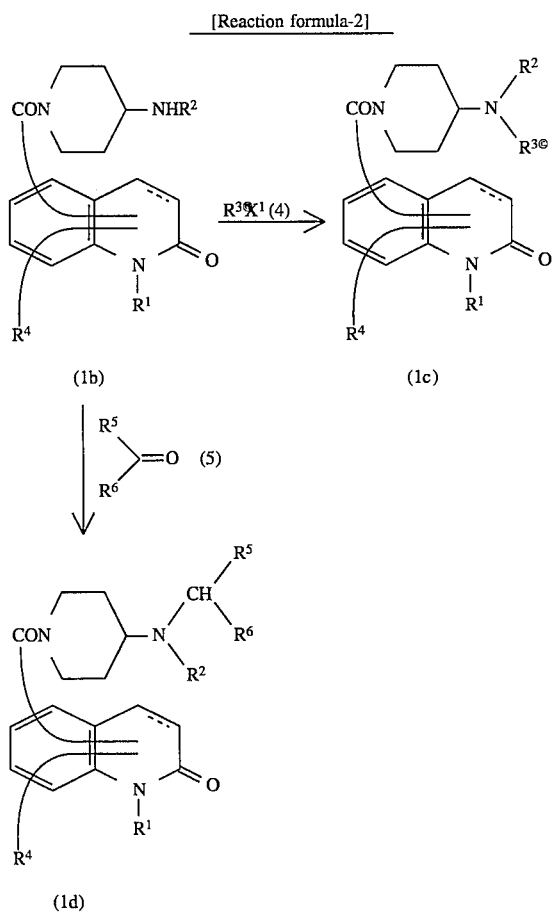

(wherein, $R^1$, $R^2$, $R^4$ and the carbon-carbon bond between 3- and 4-positions in the carbostyril skeleton are the same as defined above; $R^{3'}$ is the same as the above-mentioned $R^3$ but excludes a case that it is a hydrogen atom; $R^5$ represents a hydrogen atom or a lower alkyl group; $R^6$ represents a hydrogen atom, a lower alkyl group, a phenyl group, a phenyl-lower alkyl group, a phenylthio-lower alkyl group or a phenoxy-lower alkyl group which may have, on the phenyl ring, 1–3 substituents selected from the group consisting of halogen atoms and lower alkoxy groups; and $X^1$ represents a halogen atom, a lower alkanesulfonyloxy group, an arylsulfonyloxy group or an aralkylsulfonyloxy group.

In the compound represented by the above general formula (4), specific examples of the halogen atom represented by $X^1$ are chlorine, fluorine, bromine and iodine atoms; specific examples of the lower alkanesulfonyloxy group are methanesulfonyloxy, ethanesulfonyloxy, propanesulfonyloxy, isopropanesulfonyloxy, butanesulfonyloxy, tert-butanesulfonyloxy, pentanesulfonyloxy and hexanesulfonyloxy; specific examples of the arylsulfonyloxy group are substituted or unsubstituted arylsulfonyloxy groups such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy and α-naphthylsulfonyloxy groups and the like; and specific examples of the aralkylsulfonyloxy group are substituted or unsubstituted aralkylsulfonyloxy groups such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy and α-naphthylmethylsulfonyloxy groups and the like.

The reaction of the compound of general formula (1b) with the compound of general formula (4) can be carried out using the same procedure and conditions as employed in the above-mentioned process which comprises reacting a carboxylic acid halide with an amine (3). To the reaction system may be added, for example, an alkali metal halide such as sodium iodide, potassium iodide or the like.

The reaction of the compound of general formula (1b) with the compound of general formula (5) is conducted in the presence of an appropriate solvent or in the absence of any solvent, in the presence of a reducing agent. The solvent can be exemplified by water; alcohols such as methanol, ethanol, isopropanol and the like; acetic acid; ethers such as dioxane, tetrahydrofuran, diethyl ether, diglyme and the like; aromatic hydrocarbons such as benzene, toluene, xylene and the like; and mixtures thereof. The reduction method usable includes, for example, a method of using, as a reducing agent, formic acid or a hydride such as sodium boron hydride, sodium cyanoboron hydride, lithium aluminum hydride or the like, and a catalytic reduction method of using a catalytic reduction catalyst such as palladium black, palladium-carbon, platinum oxide, platinum black, Raney nickel or the like. When formic acid is used as a reducing agent, the reaction is conducted generally at room temperature to 200° C., preferably at about 50°–150° C. and is complete in about 1–10 hours. The desirable amount of formic acid used is a large excess over the compound of general formula (1b). When a hydride is used as a reducing agent, the reaction is conducted generally at –30° C. to 100° C., preferably at about 0°–70° C. and is complete in about 30 minutes to 12 hours. The desirable amount of the hydride used is generally 1–20 moles, preferably 1–5 moles per mole of the compound of general formula (1b). When the hydride as a reducing agent is, in particular, lithium aluminum hydride, it is preferable to use a solvent such as ether (e.g. dioxane, tetrahydrofuran, diethyl ether or diglyme), aromatic hydrocarbon (e.g. benzene, toluene or xylene) or the like. When a catalytic reduction catalyst is used, the reaction is conducted in a hydrogen atmosphere of generally normal pressure to 20 atm., preferably normal pressure to 10 atm. generally at –30° C. to 100° C., preferably at 0°–60° C. The desirable amount of the catalyst used is generally 0.1–40% by weight, preferably 1–20% by weight based on the compound of general formula (1b). The desirable amount of the compound (5) used is generally at least equimolar, preferably equimolar to a large excess over the compound of general formula (1b).

[Reaction formula-3]

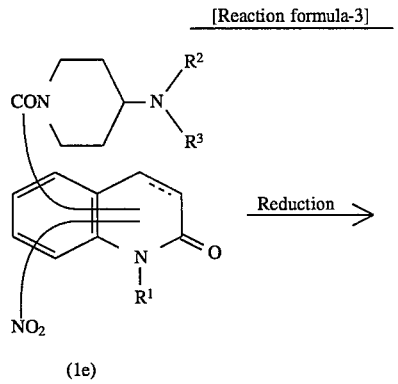

-continued
[Reaction formula-3]

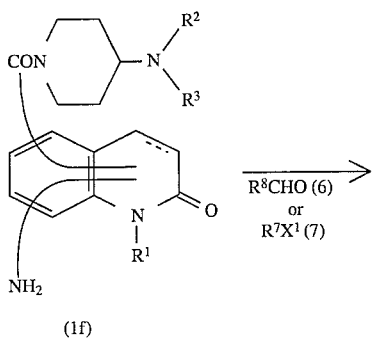

(1f)

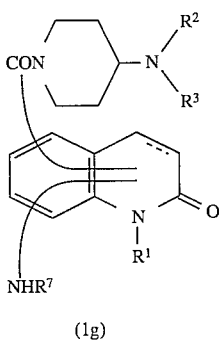

(1g)

(wherein, $R^1$ $R^2$, $R^3$, $X^1$ and the carbon-carbon bond between 3- and 4-positions in the carbostyril skeleton are the same as defined above; $R^7$ represents a phenyl-lower alkyl group; and $R^8$ represents a phenyl group or a phenyl-lower alkyl group).

The reduction of the compound (1e) is conducted, for example, (1) using a catalytic reduction catalyst in an appropriate solvent, or (2) using, as a reducing agent, a mixture between a metal or a metal salt and an acid, or between a metal or a metal salt and an alkali metal hydroxide, a sulfide, an ammonium salt or the like in an appropriate inert solvent.

When the reduction is conducted by the above method (1) using a catalytic reduction catalyst in an appropriate solvent, the solvent includes, water; acetic acid; alcohols such as methanol, ethanol, isopropanol and the like; hydrocarbons such as hexane, cyclohexane and the like; ethers such as dioxane, tetrahydrofuran, diethyl ether, diethylene glycol dimethyl ether and the like; esters such as ethyl acetate, methyl acetate and the like; aprotic polar solvents such as N,N-dimethylformamide and the like; and mixed solvents thereof. The catalytic reduction catalyst includes, for example, palladium, palladium black, palladium-carbon, platinum, platinum oxide and Raney nickel. The desirable amount of the catalyst used is generally about 0.02–1 time the amount of the starting material. The reaction temperature is generally about −20° C. to 150° C., preferably about 0°–100° C., and the hydrogen pressure is generally 1–10 atm. The reaction is complete generally in about 0.5–10 hours. An acid such as hydrochloric acid or the like may be added in the reaction.

When the reduction is conducted by the above method (2) using a reducing agent in an appropriate inert solvent, the reducing agent includes, for example, a mixture between iron, zinc, tin or stannous chloride and an acid (e.g. hydrochloric acid or sulfuric acid), and a mixture between iron, ferrous sulfate, zinc or tin and an alkali metal hydroxide (e.g. sodium hydroxide), a sulfide (e.g. ammonium sulfide), ammonia water or an ammonium salt (e.g. ammonium chloride). The solvent can be exemplified by water, acetic acid, methanol, ethanol and dioxane. The conditions for reduction can be appropriately selected depending upon the type of the reducing agent used. For example, when a mixture of stannous chloride and hydrochloric acid is used as a reducing agent, the reaction can be conducted favorably by employing a reaction temperature of about 0° C. to room temperature and a reaction time of about 0.5–10 hours. The reducing agent is used in an amount of at least 1 mole, generally 1–5 moles per mole of the starting material compound.

The reaction of the compound of general formula (1f) with the compound of general formula (6) is conducted in the absence of any solvent or in the presence of an appropriate solvent, in the presence or absence of a dehydrating agent. The solvent includes, for example, alcohols such as methanol, ethanol, isopropanol and the like; aromatic hydrocarbons such as benzene, toluene, xylene and the like; halogenated hydrocarbons such as dichloromethane, dichloroethane, chloroform, carbon tetrachloride and the like; aprotic polar solvents such as N,N-dimethylformamide, N,N-dimethylacetamide, N-methylpyrrolidone and the like; and mixed solvents thereof. The dehydrating agent includes, for example, drying agents conventionally used for drying of solvents, such as molecular sieve and the like; mineral acids such as hydrochloric acid, sulfuric acid and the like; Lewis acids such as boron trifluoride and the like; and organic acids such as p-toluenesulfonic acid and the like. The reaction is conducted generally at room temperature to 250° C., preferably at about 50°–200° C. and is complete generally in about 1–48 hours. The amount of the compound of general formula (6) used is not particularly restricted but desirably is generally at least equimolar, preferably equimolar to a large excess over the compound of general formula (1f). The desirable amount of the dehydrating agent used is generally a large excess when a drying agent is used, and is a catalytic amount when an acid is used.

The reaction of the compound (1f) with the compound (6) produces a Schiff base as an intermediate. The intermediate is reduced to convert into a compound (1g). Various methods can be employed for this reduction and, for example, a method using a hydride as a reducing agent is preferably used. The hydride includes, for example, lithium aluminum hydride, sodium boron hydride and diborane. The amount of the hydride used is generally at least 1 mole, preferably 1–10 moles per mole of the compound (1f). The reduction is conducted generally using an appropriate solvent such as water, lower alcohol (e.g. methanol, ethanol or isopropanol), ether (e.g. tetrahydrofuran, diethyl ether or diglyme) or the like generally at about −60° C. to 50° C., preferably at −30° C. to room temperature for about 10 minutes to 5 hours. When lithium aluminum hydride or diborane is used as a reducing agent, it is preferable to use an anhydrous solvent such as diethyl ether, tetrahydrofuran, diglyme or the like.

The reaction of the compound (1f) with the compound (7) is conducted under the same conditions as employed in the reaction of the compound (1b) with the compound (4) in the Reaction formula-2.

[Reaction formula-4]

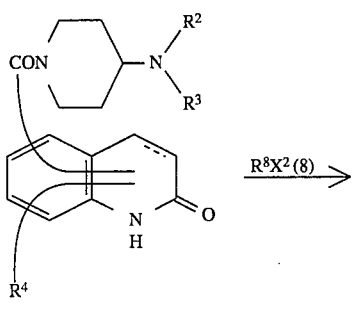

(1h)

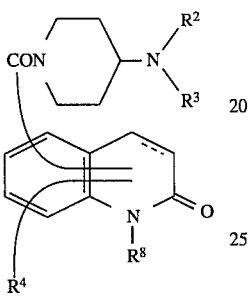

(1i)

(wherein, $R^2$, $R^3$, $R^4$ and the carbon-carbon bond between 3- and 4-positions in the carbostyril skeleton are the same as defined above; $R^8$ represents a lower alkyl group; and $X^2$ represents a halogen atom).

The reaction of the compound of general formula (1h) with the compound of general formula (8) is desirably conducted, for example, in the presence of a basic compound in an appropriate solvent. The basic compound includes, for example, sodium hydride, potassium, sodium, sodium amide and potassium amide. The solvent includes, for example, ethers such as dioxane, diethylene glycol dimethyl ether and the like; aromatic hydrocarbons such as toluene, xylene and the like; N,N-dimethylformamide; dimethyl sulfoxide; and hexamethylphosphoric triamide. The proportions of the compound (1h) and the compound (8) are not particularly restricted and can be appropriately selected from a wide range. Desirably, however, the latter is used in an amount of at least about 1 mole, preferably about 1–5 moles per mole of the former. The reaction is conducted generally at about 0°–70° C., preferably at about 0° C. to room temperature and is complete generally in about 0.5–15 hours.

[Reaction formula-5]

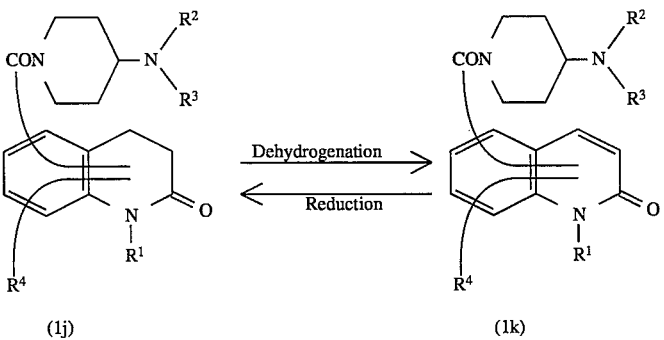

(1j)   (1k)

(wherein, $R^1$, $R^2$, $R^3$ and $R^4$ are the same as defined above).

The dehydrogenation of the compound of general formula (1j) is conducted in an appropriate solvent using a dehydrogenating agent. The dehydrogenating agent includes, for example, benzoquinones such as 2,3-dichloro-5,6-dicyanobenzoquinone, chloranil (2,3,5,6-tetrachlorobenzoquinone) and the like; halogenating agents such as N-bromosuccin- imide, N-chlorosuccinimide, bromine and the like; selenium dioxide; palladium-carbon; palladium black;

palladium oxide; and Raney nickel. The amount of the halogenating agent used is not particularly restricted and can be appropriately selected from a wide range, but is generally 1–5 moles, preferably 1–2 moles per mole of the compound (1j). It desirably is an ordinary catalytic amount when palladiumcarbon, palladium black, palladium oxide, Raney nickel or the like is used. The solvent can be exemplified by ethers such as dioxane, tetrahydrofuran, methoxyethanol, dimethoxymethane and the like; aromatic hydrocarbons such as benzene, toluene, xylene, cumene and the like; halogenated hydrocarbons such as dichloromethane, dichloroethane, chloroform, carbon tetrachloride and the like; alcohols such as butanol, amyl alcohol, hexanol and the like; protic polar solvents such as acetic acid and the like; and aprotic polar solvents such as dimethylformamide, dimethyl sulfoxide, hexamethylphosphoric triamide and the like. The reaction is conducted generally at about room temperature to 300° C., preferably at room temperature to 200° C. and is complete generally in about 1–40 hours. A catalytic amount of a peracid anhydride such as benzoyl peroxide or the like may be added to the reaction system.

The reduction of the compound of general formula (1k) is conducted under the same conditions as used in ordinary catalytic reductions. The catalyst used can be exemplified by metals such as palladium, palladium-carbon, platinum, Raney nickel and the like. These metals are used in an ordinary catalytic amount. The solvent used includes, for example, methanol, ethanol, isopropanol, dioxane, tetrahydrofuran, hexane, cyclohexane, acetic acid and ethyl acetate. The reduction may be conducted at normal pressure or under pressure but is desirably conducted generally at normal pressure to 20 kg/cm², preferably at normal pressure to 10 kg/cm². The reaction temperature is generally about 0°–150° C., preferably room temperature to 100° C.

Compounds of general formula (1) wherein $R^1$ is a hydrogen atom and the carbon-carbon bond between 3- and 4-position in the carbostyril skeleton is a double bond, can take lactam-lactim tautomerism as shown in the following Reaction formula-6.

[Reaction formula-6]

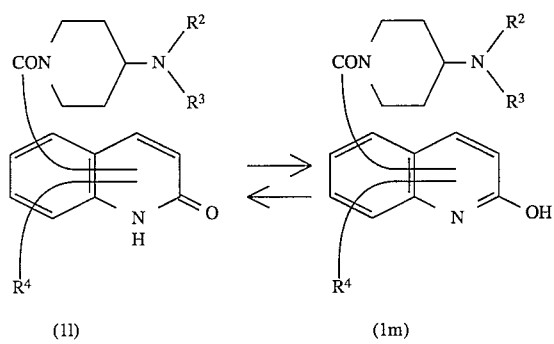

(wherein, $R^2$, $R^3$ and $R^4$ are the same as defined above).

The compound (2), which is a starting material for the compound (1), can be produced, for example, by processes represented by the following Reaction formulas -7 to -15.

[Reaction formula-7]

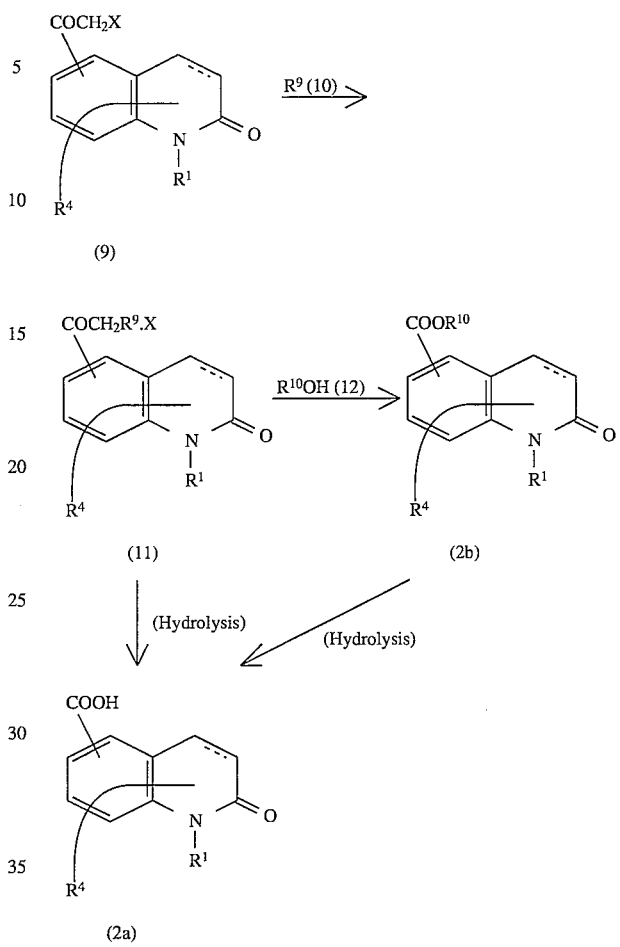

(wherein, $R^1$, $R^4$, X and the carbon-carbon bond between 3- and 4-positions in the carbostyril skeleton are the same as defined above; $R^9$ represents a nitrogen-containing heterocycle residue; and $R^{10}$ represents a lower alkyl group).

In the Reaction formula-7, the reaction of the compound (9) with the nitrogen-containing heterocycle residue (10) is conducted in an appropriate solvent or in the absence of any solvent. The solvent can be any inert solvent which does not adversely affect the reaction. It includes, for example, halogenated solvents such as chloroform, methylene chloride, dichloroethane, carbon tetrachloride and the like; ethers such as diethyl ether, tetrahydrofuran, dioxane, dimethoxyethane and the like; alcohols such as methanol, ethanol, isopropanol, butanol and the like; esters such as methyl acetate, ethyl acetate and the like; aprotic polar solvents such as N,N-dimethylformamide, dimethyl sulfoxide, hexamethylphosphoric triamide and the like; and acetonitrile. The nitrogen-containing heterocycle residue can be exemplified by pyridine and quinoline. The amount of the nitrogen-containing heterocycle residue used is at least equimolar, preferably a large excess over the compound (9). The reaction is conducted at 50°–200° C., preferably at 70°–150° C. and is complete in about 0.5–10 hours.

The hydrolysis of the resulting compound (11) is conducted by treating the compound (11) in water in the presence of an inorganic base such as sodium hydroxide, potassium hydroxide or the like at room temperature to 150° C. for about 0.5–10 hours.

The esterification of the compound (11) with the compound (12) is conducted by reacting them in the presence of a basic compound in the presence or absence of a solvent. The solvent can be exemplified by halogenated hydrocarbons such as methylene chloride, chloroform, dichloroethane and the like; aromatic hydrocarbons such as benzene, toluene, xylene and the like; ethers such as diethyl ether, tetrahydrofuran, dioxane, dimethoxyethane and the like; and aprotic polar solvents such as N,N-dimethylformamide, dimethyl sulfoxide, hexamethylphosphoric triamide and the like. The basic compound can be exemplified by organic bases such as triethylamine, trimethylamine, pyridine, N,N-dimethylaniline, N-methylmorpholine, 4-dimethylaminopyridine, 1,5-diazabicyclo[4.3.0]nonene-5 (DBN), 1,5-diazabicyclo[5.4.0]undecene-5 (DBU), 1,4-diazabicyclo[2.2.2]octane (DABCO) and the like; and inorganic bases such as potassium carbonate, sodium carbonate, potassium hydrogencarbonate, sodium hydrogencarbonate and the like. The desirable amount of the basic compound used is at least 1 mole, preferably 1–1.5 moles per mole of the compound of general formula (11). The amount of the compound (12) used is at least equimolar, generally a large excess over the compound of general formula (11). The reaction is conducted generally at room temperature to 150° C., preferably at about 50°–100° C. and is complete generally in 30 minutes to 10 hours.

The hydrolysis of the compound (2b) is desirably conducted in the presence of an acid or a basic compound in water, an alcohol (e.g. ethanol, methanol or propanol) or a mixed solvent thereof. The acid can be exemplified by mineral acids such as hydrochloric acid, sulfuric acid and the like, and the basic compound can be exemplified by potassium carbonate, sodium carbonate, sodium hydrogencarbonate, sodium hydroxide and potassium hydroxide. The amount of the acid or basic compound used is generally a large excess over the compound of general formula (2b), preferably 1–5 moles per mole of the compound (2b).

The reaction is conducted generally at room temperature to 200° C., preferably at about room temperature to 150° C. and is complete generally in about 1 hour to 4 days.

[Reaction formula-8]

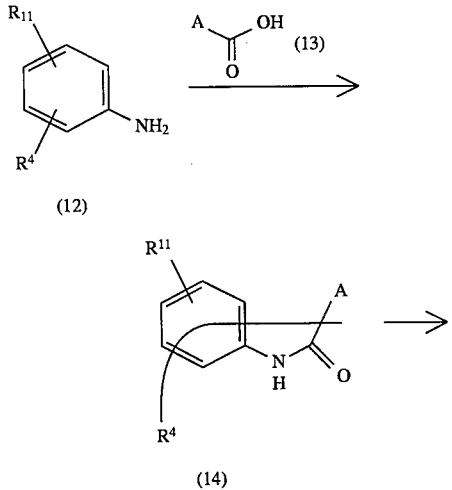

-continued
[Reaction formula-8]

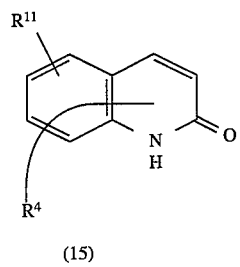

(15)

[wherein, $R^4$ is the same as defined above; $R^{11}$ represents a carboxyl group or a carbamoyl group; and A represents a group of the formula: —CH=CHR$^{12}$ ($R^{12}$ is a lower alkoxy group, a phenyl group or a halogen atom) or a group of the formula:

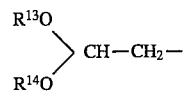

($R^{13}$ and $R^{14}$ each represent a lower alkyl group). In the compound (14), $R^4$ may bond to A and, in the starting materials, $R^4$ may bond to the benzene ring of the compound (12) or to A of the compound (13)].

The reaction of the compound (12) with the compound (13) is conducted under the same conditions as employed in the reaction of the compound (2) with the compound (3) in the Reaction formula-1.

The cyclization of the compound of general formula (14) is conducted in the presence of an acid in the absence of any solvent or in the presence of an appropriate solvent. The acid is not particularly restricted and can be an ordinary inorganic or organic acid. Specific examples of the acid are inorganic acids such as hydrochloric acid, hydrobromic acid, sulfuric acid and the like; Lewis acids such as aluminum chloride, boron trifluoride, titanium tetrachloride and the like; and organic acids such as formic acid, acetic acid, ethanesulfonic acid, p-toluenesulfonic acid and the like. Of these acids, preferable are hydrochloric acid, hydrobromic acid and sulfuric acid. The desirable amount of the acid used is generally at least equal to the weight of the compound of general formula (14), preferably 5–50 times said weight. The solvent can be any ordinary inert solvent and can be exemplified by water, lower alcohols (e.g. methanol, ethanol and propanol), ethers (e.g. dioxane and tetrahydrofuran), aromatic hydrocarbons (e.g. benzene, chlorobenzene and toluene), halogenated hydrocarbons (e.g. methylene chloride, chloroform and carbon tetrachloride), acetone, dimethyl sulfoxide, dimethylformamide and hexamethylphosphoric triamide. The reaction is conducted generally at about 0°–200° C., preferably at about room temperature to 150° C. and is complete generally in about 5 minutes to 6 hours.

A compound of general formula (15) wherein R11 is a carbamoyl group, can be converted to a compound of general formula (15) wherein R11 is a carboxyl group, by hydrolyzing the former under the same conditions as employed in the hydrolysis of the compound (2b) in the Reaction formula-7.

[Reaction formula-9]

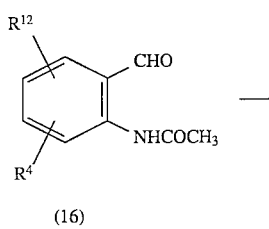

(16)

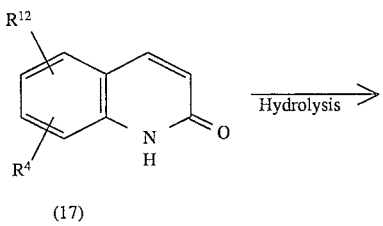

(17)

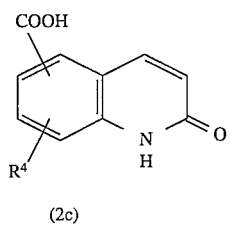

(2c)

(wherein, R⁴ is the same as defined above; and $R^{12}$ represents a lower alkoxycarbonyl group).

The reaction for converting the compound (16) into a compound (17) can be conducted in the presence of a basic compound in an appropriate solvent. The basic compound can be a wide range of compounds such as inorganic bases (e.g. sodium hydroxide, potassium carbonate, sodium hydrogencarbonate, potassium hydrogencarbonate, sodium hydride, sodium methylate and sodium ethylate), amines (e.g. triethylamine, pyridine, α-picoline, N,N-dimethylaniline, N-methylmorpholine, piperidine and pyrrolidine) and the like. The solvent includes ethers such as dioxane, tetrahydofuran, glyme, diglyme and the like; aromatic hydrocarbons such as toluene, xylene and the like; lower alcohols such as methanol, ethanol, isopropanol and the like; and polar solvents such as dimethylformamide, dimethyl sulfoxide and the like. The reaction is conducted at room temperature to 150° C., preferably at 60°–120° C. for about 1–24 hours.

The hydrolysis of the compound (17) is conducted under the same conditions as employed in the hydrolysis of the compound (2b) in the Reaction formula-7.

[Reaction formula-10]

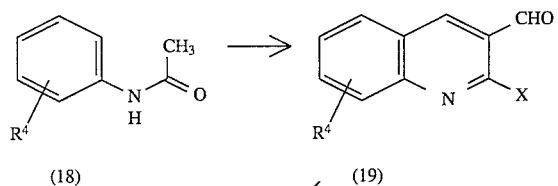

(18)    (19)

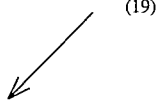

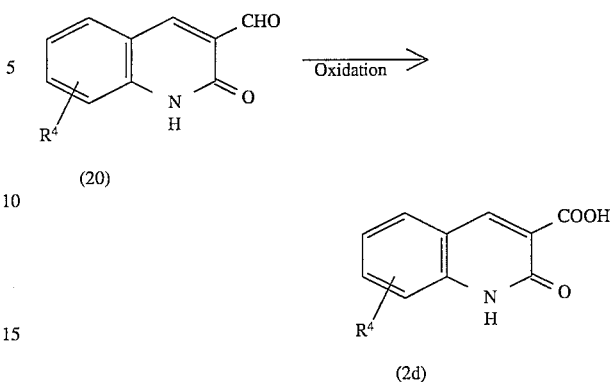

(wherein, R⁴ and X are the same as defined above).

In the above reaction formula, the reaction for converting the compound (18) into a compound (19) by ring closure is conducted in the presence of an N,N-substituted formamide and an acid catalyst (the combination of these two reagents are generally called "Vilsmeier reagent") in an appropriate solvent or in the absence of any solvent. The N,N-substituted formamide can be exemplified by N,N-di-methylformamide, N,N-diethylformamide, N-methyl-N-ethylformamide and N-methyl-N-phenylformamide. The acid catalyst can be exemplified by phosphorus oxychloride, thionyl chloride and phosgene. The solvent can be exemplified by halogenated hydrocarbons such as chloroform, 1,2-dichloroethane, 1,2-dichloroethylene and the like, and aromatic hydrocarbons such as chlorobenzene, 1,2-dichlorobenzene and the like. The desirable amounts of the N,N-substituted formamide and acid catalyst used are generally each a large excess over the compound of general formula (18), preferably 2–5 moles (the N,N-substituted formamide) and 5–10 moles (the acid catalyst) per mole of the compound (18). The reaction is desirably conducted generally at 0°–150° C., preferably at about 50°–100° C. and is complete in about 3–24 hours.

The reaction for converting the compound (19) into a compound (20) is conducted under the same conditions as employed in the hydrolysis of the compound (B) in the process of the Reaction formula-1.

The oxidation of the compound of general formula (20) is carried out in the presence of an appropriate oxidizing agent in a solvent. The oxidizing agent can be exemplified by metal salts such as chromium trioxide, sodium bichromate, potassium permanganate, silver oxide and the like; peracids such as hydrogen peroxide, peracetic acid, trifluoroperacetic acid, perbenzoic acid, m-chloroperbenzoic acid and the like; and mineral acids such as nitric acid and the like. The solvent can be exemplified by water; alcohols such as methanol, ethanol, propanol, butanol, tert-butanol and the like; ethers such as diethyl ether, tetrahydrofuran and the like; aromatic hydrocarbons such as benzene, toluene, xylene and the like; acetone; pyridine; acetic acid; and mixed solvents of two or more of the above. When a metal salt is used as the oxidizing agent, the reaction can be allowed to proceed favorably by using, as a catalyst, a base such as sodium hydroxide, potassium hydroxide and the like or an acid such as sulfuric acid and the like. The desirable amount of the oxidizing agent used is generally a large excess over the compound of general formula (20). The reaction is conducted generally at 0°–150° C., preferably at about room temperature to 100° C. for about 1–10 hours.

[Reaction formula-11]

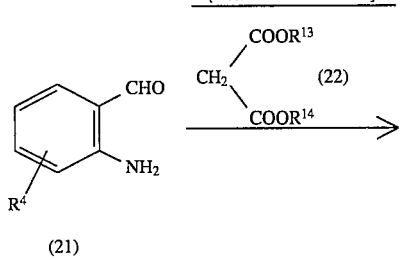

(wherein, $R^4$ is the same as defined above, and $R^{13}$ and $R^{14}$ each represent a hydrogen atom or a lower alkyl group).

The reaction of the compound (21) with the compound (22) can be conducted in the presence of a basic compound in an appropriate solvent. The basic compound and the solvent can be any basic compound and any solvent both used in the reaction for converting the compound (16) into a compound (17) in the Reaction formula-9. The reaction is conducted at room temperature to 150° C., preferably at 60°–120° C. for about 1–24 hours. The proportions of the compound (21) and the compound (22) are not particularly restricted, but the latter is used in an amount of generally at equimolar to a large excess, preferably 1–5 moles per mole of the former.

[Reaction formula-12]

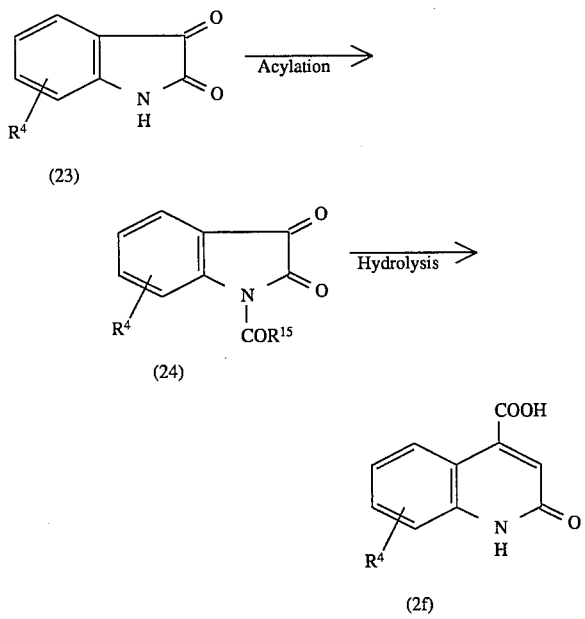

(wherein, $R^4$ is the same as defined above, and $R^{15}$ represents a lower alkyl group).

In the above process, a compound (23) is reacted with $R^{15}COX$ or $(R^{15}CO)_2O$ ($R^{15}$ and X are the same as defined above) to obtain a compound (24), and the compound (24) is hydrolyzed to obtain a compound (2f).

The reaction of the compound (23) with R15COX or $(R^{15}CO)_2O$ is conducted in the presence or absence of a basic compound. The basic compound can be exemplified by alkali metals such as metallic sodium, metallic potassium and the like; hydroxides, carbonates and bicarbonates of said alkali metals; and amine compounds such as pyridine, piperidine and the like. The reaction proceeds in the presence or absence of a solvent. The solvent includes, for example, ketones such as acetone, methyl ethyl ketone and the like; ethers such as diethyl ether, dioxane and the like; aromatic hydrocarbons such as benzene, toluene, xylene and the like; water; and pyridine. The amount of $R^{15}COX$ or $(R^{15}CO)_2O$ used is at least equimolar, generally equimolar to a large excess over the compound of general formula (23). The reaction proceeds at 0°–200° C., but is preferably conducted generally at 0°–150° C. The reaction time is about 0.5–10 hours.

The hydrolysis of the compound of general formula (24) is conducted by heating the compound in an aqueous solution in the presence of an inorganic basic compound such as potassium hydroxide, sodium hydroxide, sodium carbonate, potassium carbonate, sodium hydrogencarbonate or the like generally at 50°–150° C., preferably at 70°–100° C. for about 0.5–10 hours.

[Reaction formula-13]

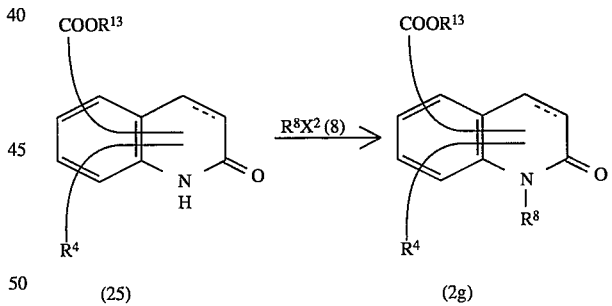

(wherein, $R^4$, $R^{13}$, $R^8$, $X^2$ and the carbon-carbon bond between 3- and 4-positions in the carbostyril skeleton are the same as defined above).

The reaction of the compound (25) with the compound (8) is conducted under the same conditions as employed in the reaction of the compound (1h) with the compound (8) in the Reaction formula-4.

[Reaction formula-14]

(2h) ⇌ (Dehydrogenation / Reduction) (2i)

(wherein, $R^1$, $R^4$ and $R^{13}$ are the same as defined above).

The dehydrogenation of the compound (2h) is conducted under the same conditions as employed in the dehydrogenation of the compound (1j) in the Reaction formula-5. The reduction of the compound (2i) is conducted under the same conditions as employed in the reduction of the compound (1k) in the Reaction formula-5. A compound (2h) or (2i) wherein $R^{13}$ is a lower alkyl group, can be converted into a compound (2h) or (2i) wherein $R^{13}$ is a hydrogen atom, by hydrolysis under the same conditions as employed in the hydrolysis of the compound (2b) in the Reaction formula-7.

A compound (2h) or (2i) wherein $R^{13}$ is a hydrogen atom, can be converted into a compound (2h) or (2i) wherein $R^{13}$ is a lower alkyl group, by esterification.

This esterification can be conducted, for example, by reacting a starting material compound with an alcohol such as methanol, ethanol, isopropanol or the like in the presence of an acid (e.g. hydrochloric acid or sulfuric acid) or a halogenating agent (e.g. thionyl chloride, phosphorus oxychloride, phosphorus pentachloride or phosphorus trichloride) generally at 0°–150° C. preferably at 50°–100° C. for about 1–10 hours.

[Reaction formula-15]

(2j) → Nitration → (2k)

(wherein, $R^1$, $R^4$, $R^{13}$ and the carbon-carbon bond between 3- and 4-positions in the carbostyril skeleton are the same as defined above).

The nitration of the compound (2j) is conducted, for example, in the absence of any solvent or in an appropriate inert solvent using a nitrating agent under the same conditions as ordinarily employed in nitration of aromatic compounds. The inert solvent can be exemplified by acetic acid, acetic anhydride and concentrated sulfuric acid. The nitrating agent can be exemplified by fuming nitric acid, concentrated nitric acid, mixed acids (mixtures of sulfuric acid, fuming sulfuric acid, phosphoric acid or acetic anhydride and nitric acid) and combinations of an alkali metal nitrate (e.g. potassium nitrate or sodium nitrate) and sulfuric acid. The amount of the nitrating agent used is at least equimolar, generally an excess over the starting material compound. The reaction is carried out generally at about −30° C. to room temperature for 5 minutes to 4 hours.

The compound (9), which is used as a starting material in the Reaction formula-7, can be produced, for example, by a process of the following Reaction formula-16.

[Reaction formula-16]

(25)

↓ $XCH_2COX^2$ (26) or $(XCH_2CO)_2O$ (27)

(9a) + (9b) + (9c)

(wherein, $R^1$, $R^4$, X, $X^2$ and the carbon-carbon bond between 3- and 4-positions in the carbostyril skeleton are the same as defined above).

The reaction of the compound of general formula (25) with the compound of general formula (26) or (27), which is generally called "Friedel-Crafts reaction" is conducted in a solvent in the presence of a Lewis acid. As the solvent, there can be favorably used those generally used in this type of reaction. The solvent can be exemplified by carbon disulfide, nitrobenzene, chlorobenzene, dichloromethane, dichloroethane, trichloroethane and tetrachloroethane. As the Lewis acid, there are preferably used those conventionally used. There can be used, for example, aluminum chloride, zinc chloride, iron chloride, tin chloride, boron tribromide, boron trifluoride and concentrated sulfuric acid. The amount of the Lewis acid used may be determined appropriately but is generally about 2–6 moles per mole of the compound of general formula (25). The amount of the compound of general formula (26) or (27) is generally at least about 1 mole, preferably 1–5 moles per mole of the compound of general formula (25). The reaction temperature may be appropriately selected but generally is about 20°–120° C., preferably about 40°–70° C. The reaction time varies depending upon the starting material, catalyst, reaction temperature, etc. used but generally about 0.5–24 hours.

The carbostyril derivatives represented by general formula (1) according to the present invention can each form an acid addition salt easily by being reacted with a pharmacologically acceptable acid. The acid can be exemplified by inorganic acids such as hydrochloric acid, sulfuric acid, phosphoric acid, hydrobromic acid and the like, and organic acids such as oxalic acid, maleic acid, fumaric acid, malic acid, tartaric acid, citric acid, benzoic acid and the like.

Of the present carbostyril derivatives represented by general formula (1), those having an acidic group can each form a salt easily by being reacted with a pharmacologically acceptable basic compound. The basic compound can be exemplified by sodium hydroxide, potassium hydroxide, calcium hydroxide, sodium carbonate and potassium hydrogen carbonate.

Each of the intended compounds obtained by the above reaction formulas can be easily separated from the reaction system and purified by ordinary means. The means for separation can be exemplified by solvent extraction, dilution, recrystallization, column chromatography and preparative thin-layer chromatography.

Needless to say, the present carbostyril derivatives of general formula (1) include optical isomers.

Each of the compounds of general formula (1) is used generally in the form of ordinary pharmaceutical preparation. The pharmaceutical preparation is prepared by using diluents or excipients ordinarily used, such as filler, bulking agent, binder, humectant, disintegrator, surfactant, lubricant and the like. The pharmaceutical preparation can be prepared in various forms depending upon the purpose of remedy, and the typical forms include tablets, pills, a powder, a solution, a suspension, an emulsion, granules, an ointment, suppositories, an injection (e.g. solution or suspension), etc. In preparing tablets, there can be used various carriers exemplified by excipients such as lactose, white sugar, sodium chloride, glucose, urea, starch, calcium carbonate, kaolin, crystalline cellulose, silicic acid and the like; binders such as water, ethanol, propanol, simple syrup, lactose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like.

The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets. In preparing pills, there can be used various carriers exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like. In preparing suppositories, there can be used carriers exemplified by a polyethylene glycol, cacao butter, a higher alcohol, a higher alcohol ester, gelatin and a semisynthetic glyceride. Capsules can be prepared generally by mixing the present compound with various carriers mentioned above and filling the mixture into a hard gelatin capsule or a soft capsule according to an ordinary method. In preparing an injection (solution, emulsion or suspension), it is sterilized and is preferably made isotonic to the blood. In preparing the solution, emulsion or suspension, there can be used diluents such as water, ethyl alcohol, polyethylene glycol, propylene glycol, ethoxylated isostearyl alcohol, polyoxyisostearyl alcohol and polyoxyethylene sorbitanfatty acid esters. In this case, the injection may contain sodium chloride, glucose or glycerine in an amount sufficient to make the injection isotonic, and may further contain a solubilizing agent, a buffer solution, a soothing agent, etc. all ordinarily used. The pharmaceutical preparation may furthermore contain, as necessary, a coloring agent, a preservative, a perfume, a flavoring agent, a sweetening agent and other drugs. In preparing the present pharmaceutical preparation in the form of a paste, a cream or a gel, there can be used diluents such as white petrolatum, paraffin, glycerin, cellulose derivatives, polyethylene glycol, silicon, bentonite and the like.

The amount of the present compound to be contained in the pharmaceutical preparation of the present invention is not particularly restricted and can be appropriately selected from a wide range, but the desirable amount is generally 1–70% by weight, preferably 1–30% by weight in the pharmaceutical preparation.

The method for administering the pharmaceutical preparation is not particularly restricted. It is decided depending upon the form of preparation, the age, distinction of sex and other conditions of patient, the disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally.

The dose of the pharmaceutical preparation is appropriately selected depending upon the administration method, the age, distinction of sex and other conditions of patient, the disease condition of patient, etc., but the desirable dose is generally about 0.01–10 mg per kg of body weight per day in terms of the amount of the active ingredient, i.e. the present compound of general formula (1). The desirable content of the active ingredient in each unit of administration form is 0.1–200 mg.

[EXAMPLES]

The present invention is described more specifically below with reference to Preparation Examples, Reference Examples, Examples and Pharmacological Test.

Preparation Example-1

| | |
|---|---|
| 8-Methyl-6-{4-[N-(2-phenylethyl)-N-methylamino]-1-piperidinyl}carbonylcarbostyril | 5 mg |
| Starch | 132 mg |
| Magnesium stearate | 18 mg |
| Lactose | 45 mg |
| Total | 200 mg |

Tablets each containing the above composition in the above amount were prepared according to an ordinary method.

Preparation Example-2

| | |
|---|---|
| 1-Methyl-6-{4-[N-(2-phenylethyl)-N-methylamino]-1-piperidinyl}carbonylcarbostyril | 500 mg |
| Polyethylene glycol (molecular weight: 4000) | 0.3 g |
| Sodium chloride | 0.9 g |
| Polyoxyethylene sorbitan mono-oleate | 0.4 g |
| Sodium metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the above distilled water at 80° C. with stirring. The resulting solution was cooled to 40° C. Therein were dissolved the above compound (present compound), polyethylene glycol and polyoxyethylene sorbitan mono-oleate in this order. To the resulting solution was added the above distilled water to obtain a final volume, followed by filtration through an appropriate filter paper for sterilization. The sterile filtrate was poured into vials each in an amount of 1 ml to prepare an injection.

Reference Example 1

A suspension of 2.0 g of 4-carboxycarbostyril in 10 ml of thionyl chloride was heated to 80° C. Thereto were added 2 g of dimethylformamide and 20 ml of chloroform. The mixture was refluxed for 2 hours by heating, to give rise to a reaction. After the completion of the reaction, the reaction mixture was concentrated under reduced pressure. The residue was mixed with n-hexane. The mixture was filtered to collect a white powder.

1.0 g of potassium carbonate was added to a suspension of 1.0 g of 4-[N-methyl-N-(2-phenylethyl)amino]piperidine in 10 ml of acetone and 10 ml of water. To the mixture was added the above-obtained white powder with ice-cooling. The resulting mixture was stirred at room temperature for 1 hour to give rise to a reaction. The reaction mixture was concentrated under reduced pressure. The residue was mixed with methylene chloride. The mixture was washed with water, followed by concentration under reduced pressure. The residue was purified by a silica gel column chromatography (elutant: dichloromethane/methanol=20/1) to obtain 1.1 g of 4-{4-[N-methyl-N-(2-phenylethyl)amino]-1-piperidinyl}carbonyl-2-chloroquinoline.

$^1$H-NMR (200 MHz, CDCl$_3$) δ (ppm): 1.20–1.80 (3H, m), 1.85–2.15 (1H, m), 2.37 (3H, s), 2.50–3.15 (7H, m), 3.25–3.50 (1H, m), 4.75–5.00 (1H, m), 7.10–7.43 (6H, m), 7.53–7.68 (1H, m), 7.68–7.86 (2H, m), 8.07 (1H, d, J=8.3 Hz).

Reference Example 2

A solution of 0.4 g of benzyl alcohol in 2 ml of dimethylformamide was dropwise added to a suspension of 150 mg of sodium hydride in 5 ml of dimethylformamide with ice-cooling. The mixture was stirred at the same temperature for 30 minutes. Thereto was dropwise added 1.0 g of 4-{4-[N-methyl-N-(2-phenylethyl)amino]-1-piperidinyl)carbonyl-2-chloroquinoline in 2 ml of dimethylformamide. The mixture was stirred at room temperature for 1 hour to give rise to a reaction. The reaction mixture was poured into ice water, followed by extraction with methylene chloride. The extract was washed with water and an aqueous sodium chloride solution in this order, then dried with magnesium sulfate and concentrated under reduced pressure to obtain 1.1 g of 4-{4-[N-methyl-N-(2-phenylethyl)amino]-1-piperidinyl)carbonyl-2-benzyloxyquinoline.

$^1$H-NMR (200 MHz, CDCl$_3$) δ (ppm): 1.20–1.80 (3H, m), 1.80–2.10 (1H, m), 2.35 (3H, s), 2.55–3.10 (7H, m), 3.35–3.57 (1H, m), 4.79–4.97 (1H, m), 5.55 (2H, s), 6.87 (1H, d, J=11.1 Hz), 7.10–7.80 (13H, m), 7.89 (1H, d, J=8.0 Hz).

Reference Example 3

8.2 g of potassium carbonate was added to a suspension of 3.0 g of 4-amino-3-methylbenzoic acid in 60 ml of acetone and 60 ml of water. Thereto was dropwise added, with ice-cooling, a solution of 4.0 g of cinnamoyl chloride in 30 ml of acetone. The mixture was stirred at the same temperature for 30 minutes to give rise to a reaction. The reaction mixture was poured into ice water, and the mixture was made acidic with concentrated hydrochloric acid. The resulting precipitate was collected by filtration, washed with water, and recrystallized from methanol to obtain 2.9 g of 4-cinnamoylamino-3-methylbenzoic acid as a white powder.

$^1$H-NMR (200 MHz, DMSO-d$_6$) δ (ppm): 2.34 (3H, s), 7.08 (1H, d, J=15.8 Hz), 7.34–7.55 (3H, m), 7.55–7.88 (5H, m), 7.94 (1H, d, J=8.4 Hz), 9.53 (1H, s), 12.75 (1H, s).

Reference Example 4

7.1 g of aluminum chloride was added to a solution of 2.5 g of 4-cinnamoylamino-3-methylbenzoic acid in 12.5 ml of chlorobenzene. The mixture was stirred at 90° C. for 1 hour to give rise to a reaction. The reaction mixture was poured into ice water. The resulting precipitate was collected by filtration and dispersed in 70 ml of ethanol and 70 ml of water. The dispersion was made alkaline with a 30% aqueous sodium hydroxide solution and then treated with active carbon. The resulting material was made acidic with concentrated hydrochloric acid. The resulting precipitate was collected by filtration and then washed with hot ethanol to obtain 0.9 g of 6-carboxy-8-methylcarbostyril as a light brown powder.

$^1$H-NMR (200 MHz, DMSO-d$_6$) δ (ppm): 2.46 (3H, s), 6.57 (1H, d, J=9.4 Hz), 7.87 (1H, s), 8.04 (1H, d, J=9.4 Hz), 8.15 (1H, s), 11.17 (1H, brs), 12.83 (1H, brs).

Reference Example 5

To a solution of 62 ml of chloroacetyl chloride in 600 ml of carbon disulfide were added, with ice-cooling, 173 g of aluminum chloride and 44 g of 8-ethylcarbostyril in this order. The mixture was refluxed for 6 hours. The reaction mixture was subjected to distillation to remove carbon disulfide. The residue was poured into ice water. The mixture was stirred at room temperature overnight. The insoluble portion was collected by filtration, washed with water and dried to obtain 55 g of 6-chloroacetyl-8-ethylcarbostyril as a brown powder.

$^1$H-NMR (200 MHz, DMSO-$d_6$) δ (ppm): 1.19 (3H, t, J=7.2 Hz), 2.92 (2H, q, J=7.2 Hz), 5.19 (2H, s), 6.60 (1H, d, J=9.4 Hz), 7.91 (1H, d, J=1.6 Hz), 8.00 (1H, d, J=9.4 Hz), 8.24 (1H, d, J=1.6 Hz), 11.31 (1H, s).

Reference Example 6

55 g of 6-chloroacetyl-8-ethylcarbostyril was added to 400 ml of pyridine. The mixture was stirred at 80°–90° C. for 30 minutes, followed by cooling. The insoluble portion was collected by filtration, washed with cold ethanol and dissolved in 200 ml of water. To the solution was added 200 ml of 5N sodium hydroxide, and the mixture was stirred at 80°–90° C. for 30 minutes. After ice-cooling, the mixture was made acidic with concentrated hydrochloric acid. The resulting precipitate was collected by filtration, washed with water and recrystallized from dimethylformamide to obtain 19 g of 6-carboxy-8-ethylcarbostyril as a light brown powder having a melting point of 300° C. or more.

$^1$H-NMR (250 MHz, DMSO-$d_6$) δ (ppm): 1.12 (3H, t, J=7.5 Hz), 2.85 (2H, q, J=7.5 Hz), 6.51 (1H, d, J=9.5 Hz), 7.82 (1H, d, J=2.0 Hz), 7.99 (1H, d, J=9.5 Hz), 8.10 (1H, d, J=2.0 Hz), 11.17 (1H, brs), 12.84 (1H, brs).

By using 6-chloroacetyl-8-ethyl-3,4dihydrocarbostyril, there was obtained 6-carboxy-8-ethyl-3,4-dihydrocarbostyril as a light brown powder in the same manner as in Reference Example 6.

$^1$H-NMR (200 MHz, DMSO-$d_6$) δ (ppm): 1.13 (3H, t, J=7.4 Hz), 2.35–2.55 (2H, m), 2.69 (2H, q, J=7.4 Hz), 2.95–3.05 (2H, m), 7.64 (2H, s), 9.76 (1H, s), 12.65 (1H, brs).

Reference Example 7

By using suitable starting materials, the following compounds were obtained in the same manner as in Reference Example 5.
(1) By using chloroacetyl chloride and 8-ethyl-3,4-dihydrocarbostyril, there was obtained 6-chloro-acetyl-8-ethyl-3,4-dihydrocarbostyril as a white powder.

$^1$H-NMR (250 MHz, DMSO-$d_6$) δ (ppm): 1.12 (3H, t, J=7.7 Hz), 2.44–2.59 (2H, m), 2.70 (2H, q, J=7.7 Hz), 2.88–3.03 (2H, m), 5.10 (2H, s), 7.67 (1H, s), 7.70 (1H, s), 9.85 (1H, s).
(2) By using chloroacetyl chloride and 8-methoxy-3,4-dihydrocarbostyril, there was obtained 5-chloroacetyl-8-methoxy-3,4-dihydrocarbostyril as a white powder having a melting point of 187°–188° C.
(3) By using chloroacetyl chloride and 8-propylcarbostyril, there was obtained 6-chloroacetyl-8-propylcarbostyril as a white powder having a melting point of 244°–247° C.
(4) By using chloroacetyl chloride and 8-isopropylcarbostyril, there was obtained 6-chloroacetyl-8-isopropylcarbostyril as a light yellow powder having a melting point of 250° C. or less (decomposed).
(5) By using chloroacetyl chloride and 8-isopropyl-3,4-dihydrocarbostyril, there was obtained 6-chloroacetyl-8-isopropyl-3,4-dihydrocarbostyril as a white powder having a melting point of 224°–229° C.

Reference Example 8

By using suitable starting materials, the following compounds were obtained in the same manner as in Reference Example 6.
(1) By using 5-chloroacetyl-8-methoxy-3,4-dihydrocarbostyril, there was obtained 5-carboxy-8-methoxy-3,4-dihydrocarbostyril as a light yellow powder.

$^1$H-NMR (200 MHz, DMSO-$d_6$) δ (ppm): 2.33–2.46 (2H, m), 3.22–3.38 (2H, m), 3.85 (3H, s), 6.96 (1H, d, J=8.7 Hz), 7.56 (1H, d, J=8.7 Hz), 9.09 (1H, s).
(2) By using 6-chloroacetyl-8-propylcarbostyril, there was obtained 6-carboxy-8-propylcarbostyril as a light brown powder having a melting point of 300° C. or higher.

$^1$H-NMR (200 MHz, DMSO-$d_6$) δ (ppm): 0.93 (3H, t, J=7.2 Hz), 1.54 (2H, sextet, J=7.2 Hz), 2.88 (2H, q, J=7.2 Hz), 6.56 (1H, d, J=9.6 Hz), 7.85 (1H, d, J=1.8 Hz), 8.03 (1H, d, J=9.6 Hz), 8.15 (1H, d, J=1.8 Hz), 11.28 (1H, brs), 12.88 (1H, brs).
(3) By using 6-chloroacetyl-8-isopropylcarbostyril, there was obtained 6-carboxy-8-isopropylcarbostyril as a light brown powder having a melting point of 300° C. or higher.

$^1$H-NMR (200 MHz, DMSO-$d_6$) δ (ppm): 1.22 (3H, d, J=6.6 Hz), 3.66 (1H, septet, J=6.6 Hz), 6.57 (1H, d, J=9.6 Hz), 7.95 (1H, d, J=1.6 Hz), 8.05 (1H, d, J=9.6 Hz), 8.16 (1H, d, J=1.6 Hz), 11.21 (1H, brs), 12.91 (1H, brs).
(4) By using 6-chloroacetyl-8-isopropyl-3,4-dihydrocarbostyril, there was obtained 6-carboxy-8-isopropyl-3,4-dihydrocarbostyril as a white powder having a melting point of 280°–282° C.

Reference Example 9

5.27 g of sodium hydride was added to 400 ml of anhydrous ethanol at room temperature. The mixture was stirred for 5 minutes. Thereto were added 23.4 g of methyl 4-acetylamino-3-formyl-5-methoxybenzoate and 100 ml of ethanol in this order. The mixture was refluxed by heating, for 1 hour. The solvent in the mixture was removed by distillation. The residue was extracted with methylene chloride. The extract was washed with water and a saturated aqueous sodium chloride solution in this order, dried with anhydrous magnesium sulfate and then concentrated. The residue was washed with diethyl ether, then purified by silica gel column chromatography (elutant: methylene chloride) and washed with diethyl ether to obtain 5.75 g of 8-methoxy-6-ethoxycarobnylcarbostyril as a white powder.

$^1$H-NMR (200 MHz, CDCl$_3$) δ (ppm): 1.43 (3H, t, J=7.1 Hz), 4.04 (3H, s), 4.42 (2H, q, J=7.1 Hz), 6.71 (1H, d, J=9.6 Hz), 7.61 (1H, d, J=1.5 Hz), 7.78 (1H, d, J=9.6 Hz), 7.92 (1H, d, J=1.5 Hz), 9.37 (1H, brs).

Reference Example 10

8.09 ml of a 5N aqueous sodium hydroxide solution was added to a suspension of 2.00 g of 8-methoxy-6-ethoxycarbonylcarbostyril in ethanol. The mixture became uniform in about 1 minute. The mixture was stirred at room temperature for 4 days. The resulting precipitate was collected by filtration and dissolved in water. The solution was washed with ethyl acetate, and then was made acidic with concentrated hydrochloric acid with ice-cooling. The resulting precipitate was collected by filtration to obtain 1.62 g of 8-methoxy-6-carboxycarbostyril as a white powder.

$^1$H-NMR (200 MHz, DMSO-d$_6$) δ (ppm): 3.98 (3H, s), 6.61 (1H, d, J=9.6 Hz), 7.57 (1H, d, J=1.6 Hz), 7.96 (1H, d, J=1.6 Hz), 8.04 (1H, d, J=9.6 Hz), 11.22 (1H, brs), 12.97 (1H, brs).

Reference Example 11

0.12 g of 10% Pd-C was added to 20 ml of an acetic acid solution containing 1.20 g of 8-methoxy-6-ethoxycarbonylcarbostyril. The mixture was subjected to hydrogenation at 90° C. at normal pressure for 1 hour. The catalyst in the reaction mixture was removed by filtration. The filtrate was subjected to distillation to remove the solvent. The residue was purified by a silica gel column chromatography (elutant: chloroform) and recrystallized from chloroform-diethyl ether to obtain 0.85 g of 8-methoxy-6-ethoxycarbonyl-3,4-dihydrocarbostyril as a white powder.

$^1$H-NMR (200 MHz, CDCl$_3$) δ (ppm): 1.40 (3H, t, J=7.1 Hz), 2.59–2.76 (2H, m), 2.93–3.12 (2H, m), 3.93 (3H, s), 4.37 (2H, q, J=7.1 Hz), 7.45 (1H, d, J=1.4 Hz), 7.53 (1H, d, J=1.4 Hz), 7.91 (1H, brs).

Reference Example 12

By using 0.85 g of 8-methoxy-6-ethoxycarbonyl-3,4-dihydrocarbostyril and in the same manner as in Reference Example 10, 0.75 g of 8-methoxy-6-carboxy-3,4-dihydrocarbostyril was obtained as colorless needle-like crystals (recrystallized from methanol).

$^1$H-NMR (200 MHz, DMSO-d$_6$) δ (ppm): 2.45–2.60 (2H, m), 2.94–3.05 (2H, m), 3.84 (3H, s), 7.37 (1H, s), 7.43 (1H, s), 9.41 (1H, s), 12.71 (1H, s).

Reference Example 13

7 ml of thionyl chloride was added to a solution of 15 g of 8-nitro-6-carboxy-3,4-dihydrocarbostyril in 150 ml of methanol with ice-cooling. The mixture was refluxed by heating, for 3 hours. The reaction mixture was concentrated under reduced pressure. The residue was recrystallized from methanol to obtain 12.8 g of 8-nitro-6-methoxycarbonyl-3,4-dihydrocarbostyril as a light yellow powder.

$^1$H-NMR (250 MHz, CDCl$_3$) δ (ppm): 2.70–2.81 (2H, m), 3.13–3.24 (2H, m), 3.96 (3H, s), 8.15 (1H, d, J=1.8 Hz), 8.81 (1H, d, J=1.8 Hz), 11.40 (1H, s).

Reference Example 14

10 g of 8-ethyl-6-carboxy-3,4-dihydrocarbostyril was gradually added to a solution of 4.2 g of sodium hydride in 50 ml of dimethylformamide with ice-cooling. The mixture was stirred at room temperature for 30 minutes. Thereto was dropwise added a solution of 9.0 ml of methyl iodide in 20 ml of dimethylformamide with ice-cooling. The mixture was stirred at room temperature overnight. The reaction mixture was poured into ice water. The resulting mixture was extracted with methylene chloride. The extract was washed with water and a saturated aqueous sodium chloride solution in this order, then dried with anhydrous magnesium sulfate and concentrated under reduced pressure to remove the solvent. The residue was purified by silica gel column chromatography (elutant: methylene chloride/methanol= 100/0 to 100/5) to obtain 10.0 g of 1-methyl-8-ethyl-6-methoxycarbonyl-3,4-dihydrocarbostyril as a colorless oil.

$^1$H-NMR (200 MHz, CDCl$_3$) δ (ppm): 1.27 (3H, t, J=7.5 Hz), 2.52–2.66 (2H, m), 2.75 (2H, q, J=7.5 Hz), 2.83–2.96 (2H, m), 3.37 (3H, s), 3.91 (3H, s), 7.70 (1H, s), 7.84 (1H, s).

Reference Example 15

By using suitable starting materials, the following compounds were obtained in the same manners as in Reference Examples 13 and 14.
(1) 8-Ethyl-6-methoxycarbonyl-3,4-dihydrocarbostyril, a white powder $^1$H-NMR (200 MHz, CDCl$_3$) δ (ppm): 1.27 (3H, t, J=7.5 Hz), 2.50–2.75 (4H, m), 2.95–3.10 (2H, m), 3.90 (3H, s), 7.61 (1H, brs), 7.74 (1H, s), 7.77 (1H, s).
(2) 8-Ethyl-6-methoxycarbonylcarbostyril, a white powder $^1$H-NMR (250 MHz, CDCl$_3$) δ (ppm): 1.37 (3H, t, J=7.5 Hz), 2.88 (1H, q, J=7.5 Hz), 3.95 (3H, s), 6.70 (1H, d, J=9.6 Hz), 7.82 (1H, d, J=9.6 Hz), 8.03 (1H, s), 8.15 (1H, s), 9.54 (1H, brs).

Reference Example 16

10.7 g of N-bromosuccinimide and a catalytic amount of benzoyl peroxide were added to a solution of 2 g of 8-nitro-6-methoxycarbonyl-3,4-dihydrocarbostyril in 200 ml of chloroform. The mixture was refluxed by heating, for 4 hours. Thereto was added an additional amount (5.0 g) of N-bromosuccinimide. The resulting mixture was refluxed by heating, for 1 hour. The reaction mixture was concentrated under reduced pressure. The residue was recrystallized from ethanol two times to obtain 7.1 g of 8-nitro-6-methoxycarbonylcarbostyril as light yellow needles.

$^1$H-NMR (200 MHz, CDCl$_3$) δ (ppm): 4.02 (3H, s), 6.82 (1H, dd, J=1.9 Hz, 9.7 Hz), 7.87 (1H, d, J=9.7 Hz), 8.50–8.60 (1H, m), 9.13 (1H, d, J=1.8 Hz), 11.39 (1H, brs).

Reference Example 17

By using suitable starting materials, the following compounds were obtained in the same manner as in Reference Example 16.
(1) 4-Methyl-6-carboxycarbostyril, a light brown powder $^1$H-NMR (200 MHz, DMSO-d$_6$) δ (ppm): 2.47 (3H, s), 6.48 (1H, s), 7.36 (1H, d, J=8.6 Hz), 8.03 (1H, dd, J=1.6 Hz, 8.6 Hz), 8.25 (1H, d, J=1.6 Hz), 11.92 (1H, brs), 12.96 (1H, brs).
(2) 1-Methyl-8-ethyl-6-methoxycarbonylcarbostyril, a white powder $^1$H-NMR (200 MHz, CDCl$_3$) δ (ppm): 1.33 (3H, t, J=7.5 Hz), 3.10 (2H, q, J=7.5 Hz), 3.82 (3H, s), 3.95 (3H, s), 6.71 (1H, d, J=9.4 Hz), 7.68 (1H, d, J=9.4Hz ), 8.06 (2H, s).

Reference Example 18

By using suitable starting materials, the following compounds were obtained in the same manner as in Reference Example 10.
(1) 8-Nitro-6-carboxycarbostyril, a light yellow powder $^1$H-NMR (200 MHz, DMSO-d$_6$) δ (ppm): 6.80 (1H, d, J=9.7 Hz), 8.27 (1H, d, J=9.7 Hz), 8.71 (1H, d, J=1.9 Hz), 8.75 (1H, d, J=1.9 Hz), 11.20 (1H, brs), 13.69 (1H, brs).
(2) 1-Methyl-8-ethyl-6-carboxy-3,4-dihydrocarbostyril, a white powder $^1$H-NMR (200 MHz, CDCl$_3$) δ (ppm): 1.29 (3H, t J=7.4 Hz), 2.53–2.70 (2H, m), 2.78 (2H, q, J=7.4 Hz), 2.85–3.00 (2H, m), 3.39 (3H, s), 7.77 (1H, d, J=2 Hz), 7.91 (1H, d, J=2 Hz)
(3) 1-Methyl-8-ethyl-6-carboxycarbostyril, a white powder $^1$H-NMR (200 MHz, DMSO-d$_6$) δ (ppm): 1.23 (3H, t, J=7.4 Hz), 3.09 (2H, q, J=7.4 Hz), 3.71 (3H, s), 6.64 (1H, d, J=9.4 Hz), 7.97 (1H, d, J=2.0 Hz), 8.01 (1H, d, J=9.4 Hz), 8.15 (1H, d, J=2.0 Hz), 13.01 (1H, brs).

Reference Example 19

4.1 g of potassium carbonate was added to a solution of 2.0 g of 4-carbamoylaniline in 40 ml of acetone and 40 ml of water. To the mixture was gradually added 3.2 g of 2-methylcinnamoyl chloride with ice-cooling. The resulting mixture was stirred at room temperature overnight. The reaction mixture was mixed with water. The resulting precipitate was collected by filtration, washed with water and dried to obtain 3.2 g of N-(2-methylcinnamoyl)-4-carbamoylaniline as a white powder.

$^1$H-NMR (200 MHz, DMSO-$d_6$) δ (ppm): 2.12 (3H, s), 7.18–7.55 (7H, m), 7.70–8.00 (5H, m), 10.14 (1H, s).

Reference Example 20

9.0 g of aluminum chloride was added to a suspension of 3.0 g of N-(2-methylcinnamoyl)-4-carbamoylaniline in 20 ml of chlorobenzene. The mixture was stirred at 80°–90° C. for 4 hours and at 110° C. for 1 hour. The reaction mixture was poured into ice water. The resulting precipitate was collected by filtration, washed with water, and then added to 20 ml of concentrated hydrochloric acid, 10 ml of water and 10 ml of ethanol. The mixture was refluxed by heating, for 2 hours to give rise to a reaction. The reaction mixture was concentrated under reduced pressure. The residue was added to ice water. The mixture was made alkaline with an aqueous sodium hydroxide solution, then treated with active carbon and filtered. The filtrate was made acidic with hydrochloric acid. The resulting precipitate was collected by filtration, washed with water and dried to obtain 1.0 g of 3-methyl-6-carboxycarbostyril as a light brown powder.

$^1$H-NMR (200 MHz, DMSO-$d_6$) δ (ppm): 2.09 (3H, s), 7.33 (1H, d, J=8.6 Hz), 7.89 (1H, s), 7.96 (1H, dd, J=1.6 Hz, 8.6 Hz), 8.20 (1H, d, J=1.6 Hz), 12.03 (1H, s), 12.85 (1H, brs).

Example 1

18 ml of diethyl cyanophosphate and 14.6 ml of triethylamine were dropwise added, in this order, to a solution of 19 g of 6-carboxy-8-ethylcarbostyril and 19 g of 4-[N-methyl-N-(2-phenylethyl)amino]piperidine in 200 ml of dimethylformamide with ice-cooling. The mixture was stirred for 30 minutes with ice-cooling. The reaction mixture was poured into ice water. The mixture was extracted with ethyl acetate. The extract was washed with water, dried with anhydrous sodium sulfate and then concentrated under reduced pressure. The residue was mixed with hydrochloric acid and crystallized from ethyl acetate-ethanol. The resulting crystals were collected by filtration and recrystallized from ethanol to obtain 20 g of 6-(4-[N-methyl-N-(2-phenylethyl)amino]-1-piperidinyl)carbonyl-8-ethylcarbostyril hydrochloride as colorless prism-like crystals having a melting point of 245°–248° C.

Using suitable starting materials, the following compounds of Examples 2–42 were obtained in the same manner as in Example 1.

TABLE 1

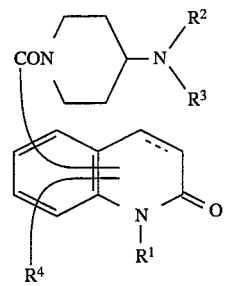

Example 2

Structural formula:

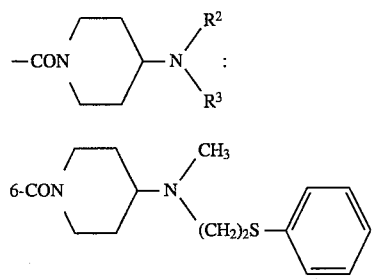

$R^1$: H
$R^4$: H
The carbon-carbon bond between 3- and 4-positions in the crbostyril skeleton: single bond
Crystal form: white powder
Salt form: hydrochloride
NMR data: 1)

Example 3

Structural formula:

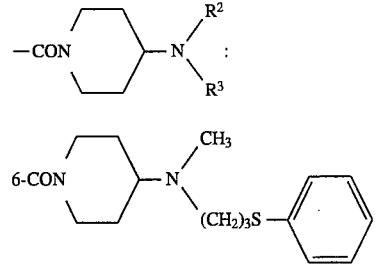

$R^1$: H
$R^4$: H
The carbon-carbon bond between 3- and 4-positions in the crbostyril skeleton: single bond
Crystal form: white powder
Salt form: hydrochloride
NMR data: 2)

TABLE 2

Example 4

Structural formula:

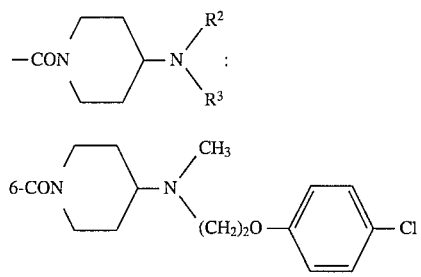

R[1]: H
R[4]: H
The carbon-carbon bond between 3- and 4-positions in the carbostyril skeleton: single bond
Crystal form: white powder
Recrystallization solvent: ethanol
Melting point (°C.): 169–171
Salt form: free Example 5

Structural formula:

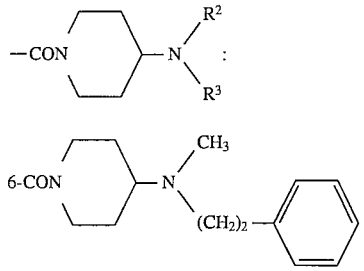

R[1]: H
R[4]: 8-CH$_3$
The carbon-carbon bond between 3- and 4-positions in the carbostyril skeleton: single bond
Crystal form: white amorphous
Salt form: hydrochloride
NMR data: 3)

Example 6

Structural formula:

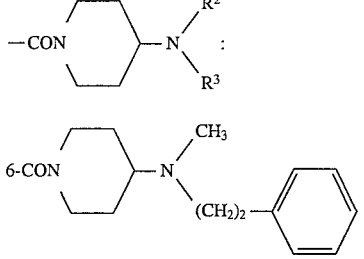

R[1]: H
R[4]: 3-CH$_3$
The carbon-carbon bond between 3- and 4-positions in the carbostyril skeleton: double bond
Crystal form: colorless prisms
Recrystallization solvent: ethyl acetate-ethanol
Melting point (°C.): 170–172
Salt form: free

TABLE 3

Example 7

Structural formula:

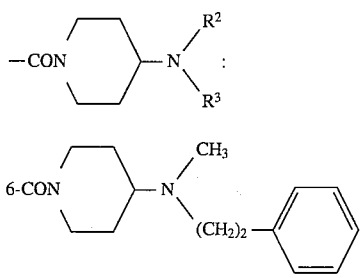

R[1]: H
R[4]: 8-CH$_3$
The carbon-carbon bond between 3- and 4-positions in the carbostyril skeleton: double bond
Crystal form: white powder
Recrystallization solvent: ethyl acetate
Melting point (°C.): 168–170 (decomposed)
Salt form: free Example 8

Structural formula:

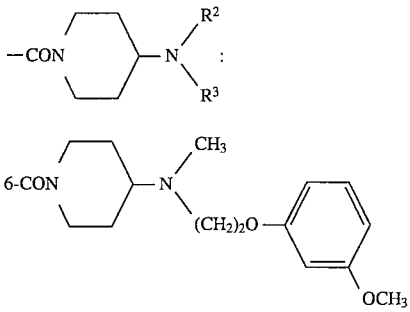

R[1]: H
R[4]: H
The carbon-carbon bond between 3- and 4-positions in the carbostyril skeleton: single bond
Crystal form: white powder
Recrystallization solvent: ethyl acetate
Melting point (°C.): 133–135
Salt form: free Example 9

Structural formula:

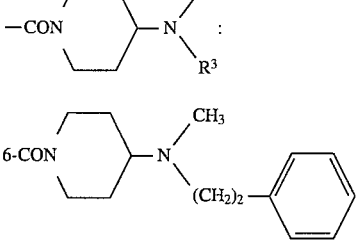

R[1]: CH$_3$
R[4]: H
The carbon-carbon bond between 3- and 4-positions in the carbostyril skeleton: double bond
Crystal form: white amorphous
Salt form: hydrochloride
NMR data: 4)

TABLE 4

Example 10

Structural formula:

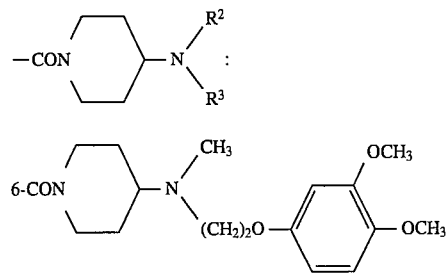

R¹: H
R⁴: H
The carbon-carbon bond between 3- and 4-positions in the carbostyril skeleton: single bond
Crystal form: white amorphous
Salt form: hydrochloride
NMR data: 15)

Example 11

Structural formula:

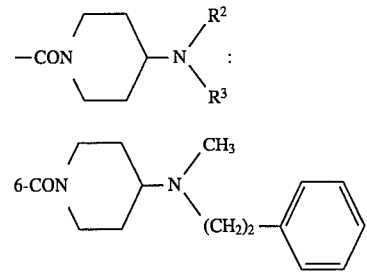

R¹: H
R⁴: 4-CH₃
The carbon-carbon bond between 3- and 4-positions in the carbostyril skeleton: single bond
Crystal form: white amorphous
Salt form: hydrochloride
NMR data: 5)

Example 12

Structural formula:

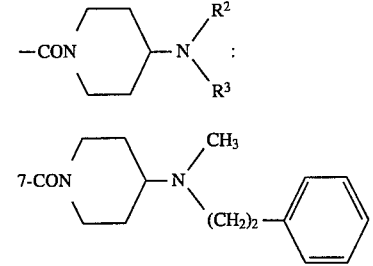

R¹: H
R⁴: H
The carbon-carbon bond between 3- and 4-positions in the carbostyril skeleton: single bond
Crystal form: white powder
Recrystallization solvent: ethanol
Melting point (°C.): 140–142
Salt form: free

TABLE 5

Example 13

Structural formula:

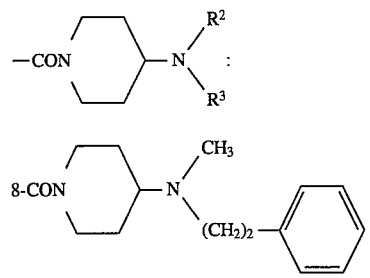

R¹: H
R⁴: H
The carbon-carbon bond between 3- and 4-positions in the carbostyril skeleton: single bond
Crystal form: white amorphous
Salt form: hydrochloride
NMR data: 6)

Example 14

Structural formula:

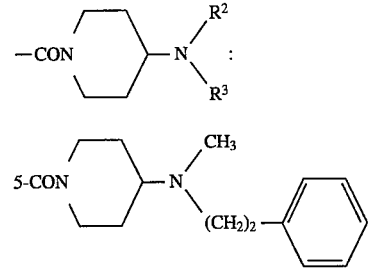

R¹: H
R⁴: H
The carbon-carbon bond between 3- and 4-positions in the carbostyril skeleton: double bond
Crystal form: white amorphous
Salt form: hydrochloride
NMR data: 7)

Example 15

Structural formula:

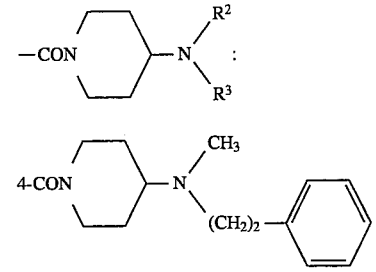

R¹: H
R⁴: H
The carbon-carbon bond between 3- and 4-positions in the carbostyril skeleton: single bond
Crystal form: white amorphous
Salt form: hydrochloride
NMR data: 8)

TABLE 6

Example 16

Structural formula:

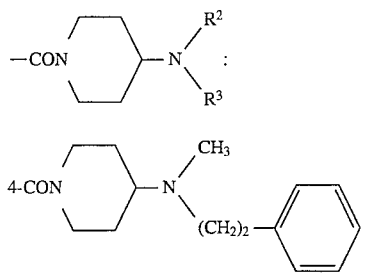

R¹: H
R⁴: H
The carbon-carbon bond between 3- and 4-positions in the carbostyril skeleton: double bond
Crystal form: white powder
Salt form: hydrochloride
Recrystallization solvent: ligroin-ethyl acetate
Melting point (°C.): 155–158
Salt form: free Example 17

Structural formula:

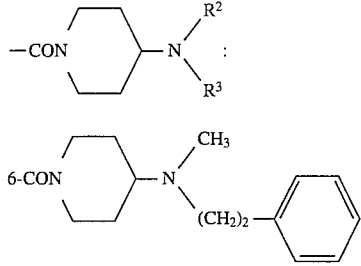

R¹: H
R⁴: 8-C$_2$H$_5$
The carbon-carbon bond between 3- and 4-positions in the carbostyril skeleton: single bond
Crystal form: white powder
Recrystallization solvent: ethanol-water
Melting point (°C.): 200–202
Salt form: oxalate Example 19

Structural formula:

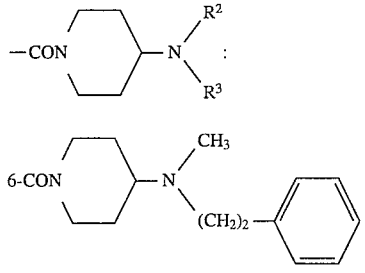

R¹: H
R⁴: 8-NO$_2$
The carbon-carbon bond between 3- and 4-positions in the carbostyril skeleton: single bond
Crystal form: yellow powder
Recrystallization solvent: ethyl acetate-diethyl ether
Melting point (°C.): 108–110
Salt form: free

TABLE 7

Example 20

Structural formula:

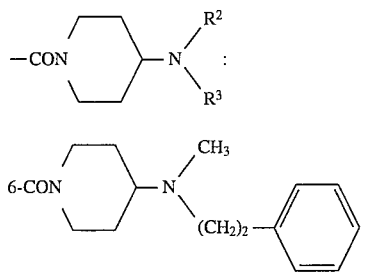

R¹: H
R⁴: 8-NO$_2$
The carbon-carbon bond between 3- and 4-positions in the carbostyril skeleton: double bond
Crystal form: yellow powder
Recrystallization solvent: ethanol
Melting point (°C.): 150–151
Salt form: hydrochloride Example 21

Structural formula:

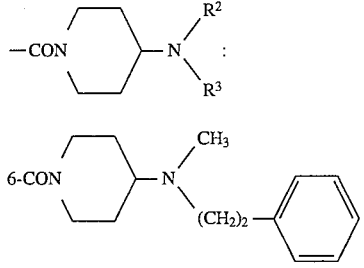

R¹: H
R⁴: 4-CH$_3$
The carbon-carbon bond between 3- and 4-positions in the carbostyril skeleton: double bond
Crystal form: white amorphous
Salt form: hydrochloride
NMR data: 9)

Example 22

Structural formula:

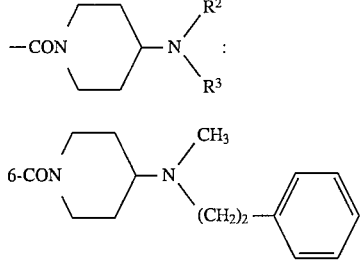

R¹: CH$_3$
R⁴: 8-C$_2$H$_5$
The carbon-carbon bond between 3- and 4-positions in the carbostyril skeleton: single bond
Crystal form: white powder
Recrystallization solvent: ethanol
Melting point (°C.): 170–180 (decomposed)
Salt form: oxalate

TABLE 8

Example 23

Structural formula:

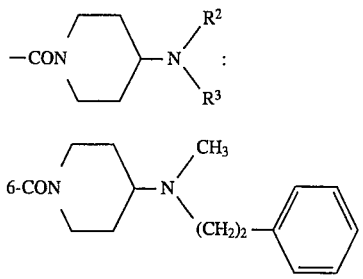

R[1]: $CH_3$
R[4]: 8-$C_2H_5$
The carbon-carbon bond between 3- and 4-positions in the carbostyril skeleton: double bond
Crystal form: white amorphous
Salt form: hydrochloride
NMR data: 10)

Example 24

Structural formula:

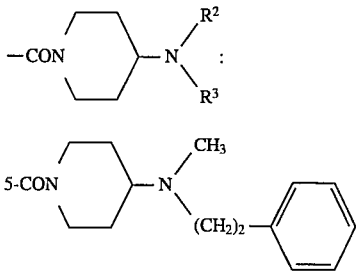

R[1]: H
R[4]: 8-$OCH_3$
The carbon-carbon bond between 3- and 4-positions in the carbostyril skeleton: single bond
Crystal form: white amorphous
Salt form: hydrochloride
NMR data: 11)

Example 25

Structural formula:

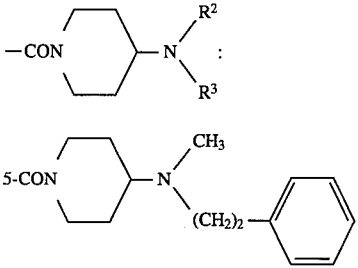

R[1]: H
R[4]: 8-$OCH_3$
The carbon-carbon bond between 3- and 4-positions in the carbostyril skeleton: double bond
Crystal form: white amorphous
Salt form: dihydrochloride
NMR data: 12)

TABLE 9

Example 26

Structural formula:

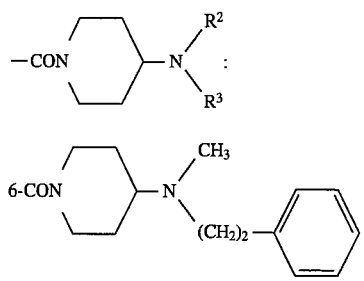

R[1]: H
R[4]: 8-$NH_2$
The carbon-carbon bond between 3- and 4-positions in the carbostyril skeleton: single bond
Crystal form: white amorphous
Salt form: free
NMR data: 13)

Example 27

Structural formula:

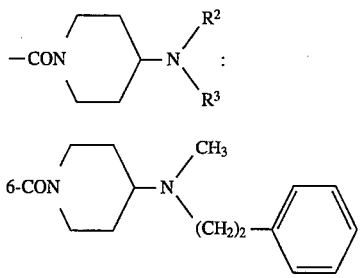

R[1]: H
R[4]: 8-$(CH_2)CH_3$
The carbon-carbon bond between 3- and 4-positions in the carbostyril skeleton: double bond
Crystal form: white powder
Recrystallization solvent: ethyl acetate-ethanol
Melting point (°C.): 233–235
Salt form: hydrochloride Example 28

Structural formula:

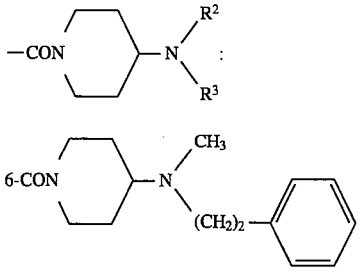

R[1]: H

R[4]: 8-CH$\begin{array}{l}CH_3\\CH_3\end{array}$

The carbon-carbon bond between 3- and 4-positions in the carbostyril skeleton: double bond
Crystal form: whitew powder TABLE 9-continued Recrystallization solvent: ethyl acetate-ethanol
Melting point (°C.): 228–231
Salt form: hydrochloride

TABLE 10

Example 29

Structural formula:

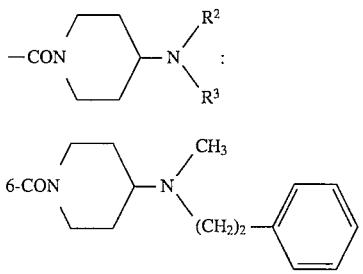

$R^1$: H

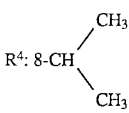

$R^4$: 8-CH(CH$_3$)CH$_3$

The carbon-carbon bond between 3- and 4-positions in
the carbostyril skeleton: single bond
Crystal form: white powder
Recrystallization solvent: ethanol
Melting point (°C.): 235–238
Salt form: hydrochloride Example 30

Structural formula:

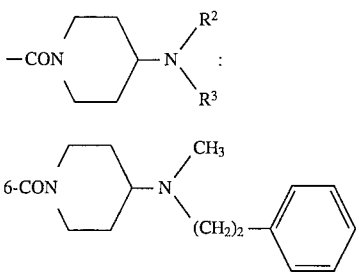

$R^1$: H

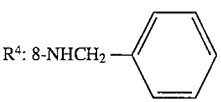

$R^4$: 8-NHCH$_2$-phenyl

The carbon-carbon bond between 3- and 4-positions in
the carbostyril skeleton: single bond
Crystal form: light yellow powder
Recrystallization solvent: ethyanol-n-hexane
Melting point (°C.): 144.5–145.5
Salt form: free TABLE 10-continued Example 31

Structural formula:

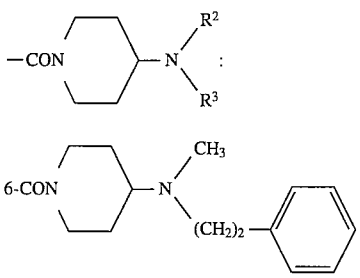

$R^1$: H
$R^4$: 7-OCH$_3$
The carbon-carbon bond between 3- and 4-positions in
the carbostyril skeleton: single bond
Crystal form: white amorphous
Salt form: hydrochloride
NMR data: 14)

TABLE 11

Example 32

Structural formula:

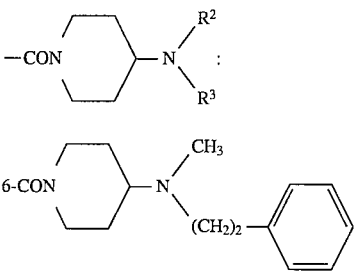

$R^1$: H
$R^4$: 7-CH$_3$
The carbon-carbon bond between 3- and 4-positions in
the carbostyril skeleton: single bond
Crystal form: white powder
Salt form: hydrochloride
Recrystallization solvent: ethanol
Melting point (°C.): 109–119 (decomposed)
Salt form: oxalate Example 33

Structural formula:

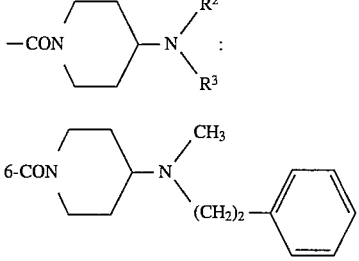

$R^1$: H
$R^4$: 7-OCH$_3$
The carbon-carbon bond between 3- and 4-positions in
the carbostyril skeleton: double bond
Crystal form: white powder
Recrystallization solvent: ethyl acetate

TABLE 11-continued

Melting point (°C.): 147–149
Salt form: free, NMR data: 18)
Example 34

Structural formula:

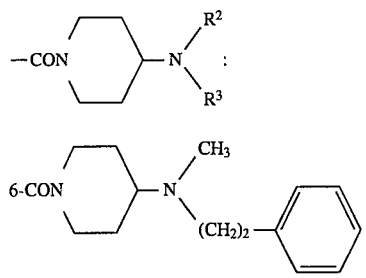

R$^1$: H
R$^4$: 8-OCH$_3$
The carbon-carbon bond between 3- and 4-positions in the carbostyril skeleton: double bond
Crystal form: white powder
Recrystallization solvent: ethanol-ethyl acetate
Melting point (°C.): 208–210
Salt form: hydrochloride

TABLE 12

Example 35

Structural formula:

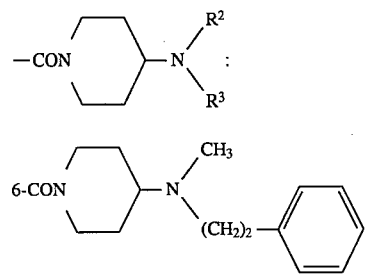

R$^1$: H
R$^4$: 8-OCH$_3$
The carbon-carbon bond between 3- and 4-positions in the carbostyril skeleton: single bond
Crystal form: white powder
Salt form: hydrochloride
Recrystallization solvent: ethanol-ethyl acetate
Melting point (°C.): 152–153
Salt form: hydrochloride
Example 36

Structural formula:

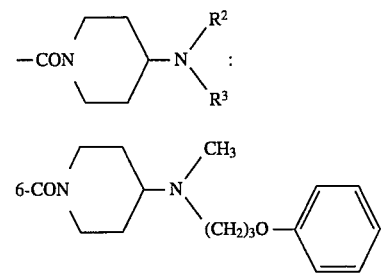

R$^1$: H
R$^4$: H
The carbon-carbon bond between 3- and 4-positions in

TABLE 12-continued the carbostyril skeleton: single bond
Crystal form: white powder
Recrystallization solvent: ethanol-water
Melting point (°C.): 238–240
Salt form: hydrochloride
Example 37

Structural formula:

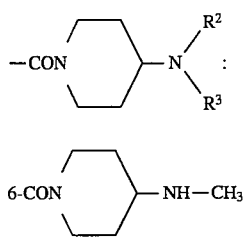

R$^1$: H
R$^4$: H
The carbon-carbon bond between 3- and 4-positions in the carbostyril skeleton: double bond
Crystal form: white powder
Recrystallization solvent: ethanol
Melting point (°C.): 280–282 (decomposed)
Salt form: hydrochloride

TABLE 13

Example 38

Structural formula:

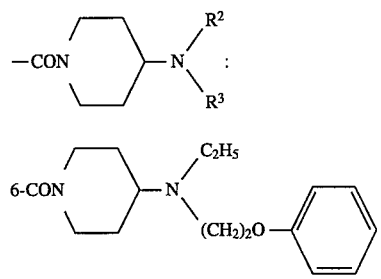

R$^1$: H
R$^4$: H
The carbon-carbon bond between 3- and 4-positions in the carbostyril skeleton: single bond
Crystal form: white amorphous
Salt form: hydrochloride
NMR data: 16)
Example 39

Structural formula:

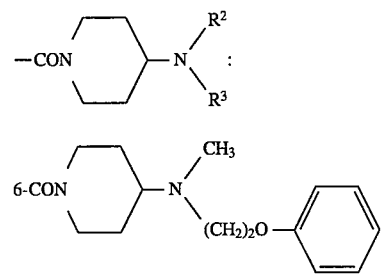

R$^1$: H
R$^4$: H
The carbon-carbon bond between 3- and 4-positions in the carbostyril skeleton: double bond TABLE 13-continued Crystal form: white powder
Recrystallization solvent: ethyl acetate-ethanol
Melting point (°C.): 143–145
Salt form: free Example 40

Structural formula:

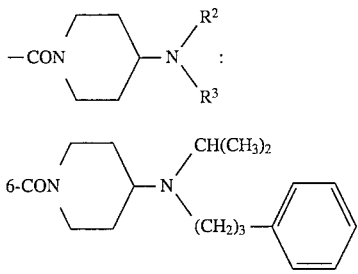

R$^1$: H
R$^4$: H
The carbon-carbon bond between 3- and 4-positions in the carbostyril skeleton: single bond
Crystal form: white amorphous
Salt form: hydrochloride
NMR data: 17)

TABLE 14

Example 41

Structural formula:

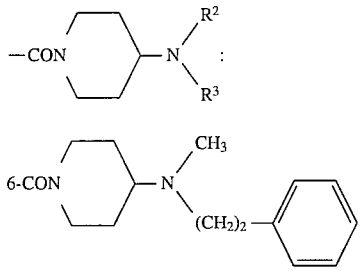

R$^1$: H
R$^4$: H
The carbon-carbon bond between 3- and 4-positions in the carbostyril skeleton: double bond
Crystal form: white powder
Salt form: hydrochloride
Recrystallization solvent: ethyl acetate-ethanol
Melting point (°C.): 157–160 (decomposed)
Salt form: free Example 42

Structural formula:

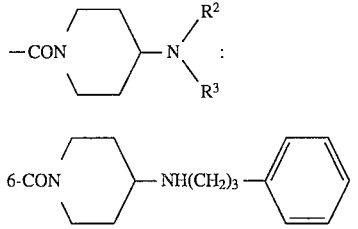

R$^1$: H
R$^4$: H
The carbon-carbon bond between 3- and 4-positions in the carbostyril skeleton: single bond TABLE 14-continued Crystal form: white powder
Recrystallization solvent: ethanol
Melting point (°C.): 255–258 (decomposed)
Salt form: hydrochloride 1) $^1$H-NMR (200 MHz, DMSO-d$_6$) δ (ppm): 1.45–1.85 (2H, m), 1.85–2.20 (2H, m), 2.38–2.58 (2H, m), 2.73 (3H, d, J=4.6 Hz), 2.80–3.08 (4H, m), 3.10–3.70 (5H, m), 3.70–4.70 (2H, m), 6.89 (1H, d, J=8.0 Hz), 7.15–7.50 (7H, m), 10.26 (1H, s), 10.90–11.20 (1H, m).

2) $^1$H-NMR (200 MHz, DMSO-d$_6$) δ (ppm): 1.50–1.80 (2H, m), 1.80–2.20 (2H, m), 2.40–2.58 (2H, m), 2.66 (3H, d, J=4.6 Hz), 2.75–3.40 (8H, m), 3.40–3.60 (1H, m), 3.60–4.90 (2H, m), 6.89 (1H, d, J=8.0 Hz), 7.13–7.45 (7H, m), 10.27 (1H, s), 10.55–10.80 (1H, m).

3) $^1$H-NMR (250 MHz, DMSO-d$_6$) δ (ppm): 1.50–1.80 (2H, m), 1.90–2.20 (2H, m), 2.23 (3H, s), 2.40–2.50 (2H, m), 2.78 (3H, d, J=4.4 Hz), 2.80–3.40 (7H, m), 3.40–4.90 (3H, m), 7.00–7.40 (7H, m), 9.60 (1H, s), 10.60–10.70 (1H, m).

4) $^1$H-NMR (200 MHz, DMSO-d$_6$) δ (ppm): 1.55–1.95 (2H, m), 1.95–2.30 (2H, m), 2.78 (3H, d, J=4.6 Hz), 2.85–3.50 (7H, m), 3.64 (3H, s), 3.50–5.00 (3H, m), 6.68 (1H, d, J=9.6 Hz), 7.20–7.45 (5H, m), 7.58 (1H, d, J=8.8 Hz), 7.68 (1H, dd, J=1.8 Hz, 8.8 Hz), 7.83 (1H, d, J=1.8 Hz), 7.96 (1H, d, J=9.6 Hz), 10.75–10.95 (1H, m).

5) $^1$H-NMR (200 MHz, DMSO-d$_6$) δ (ppm): 1.19 (3H, d, J=7.0 Hz), 1.50–1.90 (2H, m), 1.90–2.20 (2H, m), 2.27 (1H, dd, J=7.2 Hz, 16.2 Hz), 2.62 (1H, dd, J=6.0 Hz, 16.2 Hz), 2.78 (3H, d, J=4.2 Hz), 2.80–3.45 (7H, m), 2.35–4.78 (3H, m), 6.90 (1H, d, J=8.0 Hz), 7.20–7.45 (7H, 10.29 (1H, s), 10.55–10.85 (1H, m).

6) 1.50–2.30 (4H, m), 2.70–3.50 (13 Hz, m), 3.50–3.90 (2H, m), 4.40–4.80 (1H, m), 6.99 (1H, t, J=7.4 Hz), 7.15 (1H, d, J=7.4 Hz), 7.20–7.43 (6H, m), 9.37 (1H, s), 9.90–10.20 (1H, m).

7) $^1$H-NMR (200 MHz, DMSO-d$_6$) δ (ppm): 1.60–2.30 (4H, m), 2.60–3.90 (11 Hz, m), 4.65–4.85 (1H, m), 6.54 (1H, d, J=9.8 Hz), 7.00–7.90 (9H, m), 10.50–10.80 (1H, m), 11.95 (1H, s).

8) $^1$H-NMR (200 MHz, DMSO-d$_6$) δ (ppm): 1.40–1.90 (2H, m), 1.90–2.30 (2H, m), 2.40–2.80 (5H, m), 2.90–3.70 (7H, m), 4.20–4.70 (3H, m), 6.80–7.40 (9H, m), 10.06 (1H, s), 10.50–10.80 (1H, m).

9) $^1$H-NMR (200 MHz, DMSO-d$_6$) δ (ppm): 1.60–1.90 (2H, m), 1.90–2.20 (2H, m), 2.44 (3H, s), 2.79 (3H, d, J=4.6 Hz), 2.90–3.50 (6H, m), 3.50–3.90 (2H, m), 4.30–4.80 (1H, m), 6.46 (1H, s), 7.20–7.45 (6H, m), 7.58 (1H, d, J=8.4 Hz), 7.70 (1H, s), 10.50–10.80 (1H, m), 11.32 (1H, s).

10) $^1$H-NMR (200 MHz, DMSO-d$_6$) δ (ppm): 1.22 (3H, t, J=7.4 Hz ), 1.60–1.90 (2H, m ), 1.90–2.30 (2H, m), 2.79 (3H, d, J=4.6 Hz), 2.80–3.50 (8H, m), 3.50–4.10 (2H, m), 3.70 (3H, s), 4.30–4.90 (1H, m), 6.64 (1H, d, J=9.4 Hz), 7.20–7.40 (5H, m), 7.29 (1H, d, J=1.9 Hz), 7.66 (1H, d, J=1.9 Hz), 7.91 (1H, d, J=9.4 Hz).

11) $^1$H-NMR (200 MHz, DMSO-d$_6$) δ (ppm): 1.40–1.85 (2H, m), 1.85–2.30 (2H, m), 2.35–2.50 (2H, m), 2.60–2.90 (5H, m), 2.90–3.70 (8H, m), 3.82 (3H, s), 4.55–4.76 (1H, m), 6.65–7.05 (2H, m), 7.20–7.40 (6H, m), 9.20 (1H, s), 10.60–10.85 (1H, m).

12) $^1$H-NMR (200 MHz, DMSO-d$_6$) δ (ppm): 1.30–2.35 (4H, m), 2.65–3.70 (11H, m), 3.94 (3H, s), 4.60–4.80 (1H, m), 6.57 (1H, d, J=10.0 Hz), 7.00–7.45 (8H, m), 7.50–7.90 (1H, m), 10.65–10.90 (1H, m), 11.03 (1H, s).

13) $^1$H-NMR (200 MHz, CDCl$_3$) δ (ppm): 1.30–1.67 (2H, m), 1.67–2.00 (2H, m), 2.37 (3H, s), 2.53–3.20 (10H, m), 3.83–4.30 (2H, m), 4.45–4.90 (1H, m), 6.65 (2H, brs), 7.13–7.47 (5H, m), 9.75 (1H, brs).

14) $^1$H-NMR (200 MHz, DMSO-d$_6$) δ (ppm): 1.35–1.85 (2H, m), 1.85–2.33 (2H, m), 2.33–2.45 (2H, m), 2.57–2.88 (6H, m), 2.88–3.70 (7H, m), 3.72 (3H, brs), 4.50–4.80 (1H, m), 6.57 (1H, s), 6.90–7.13 (1H, m), 7.15–7.40 (5H, m), 10.14 (1H, s), 10.80–11.25 (1H, m).

15) $^1$H-NMR (200 MHz, DMSO-d$_6$) δ (ppm): 1.50–1.85 (2H, m), 1.90–2.25 (2H, m), 2.40–2.55 (2H, m), 2.70–3.15 (7H, m), 3.30–3.49 (1H, m), 3.49–3.80 (2H, m), 3.68 (3H, s), 3.74 (3H, s), 3.80–4.80 (4H, m), 6.50 (1H, dd, J=2.8 Hz, 9.0 Hz), 6.62 (1H, d, J=2.8 Hz), 6.82–6.95 (2H, m), 7.16–7.30 (2H, m), 10.26 (1H, s), 10.34–10.50 (1H, m).

16) $^1$H-NMR (200 MHz, DMSO-d$_6$) δ (ppm): 1.31 (3H, t, J=7.0 Hz), 1.56–1.90 (2H, m), 1.95–2.25 (2H, m), 2.80–3.15 (4H, m), 3.15–3.85 (7H, m), 3.85–4.70 (4H, m), 6.89 (1H, d, J=8.0 Hz), 6.94–7.10 (3H, m), 7.16–7.45 (4H, m), 9.75–10.00 (1H, m), 10.27 (1H, s).

17) $^1$H-NMR (250 MHz, DMSO-d$_6$) δ (ppm): 1.22 (3H, d, J=6.3 Hz), 1.29 (3H, d, J=6.3 Hz), 1.60–1.82 (2H, m), 1.82–2.20 (4H, m), 2.40–2.75 (3H, m), 2.75–3.45 (7H, m), 3.45–3.80 (2H, m), 3.80–4.70 (2H, m), 6.89 (1H, d, J=8.0 Hz), 7.12–7.40 (7H, m), 9.32–9.50 (1H, m), 10.28 (1H, s).

18) $^1$H-NMR (200 MHz, DMSO-d$_6$) δ (ppm): 1.20–1.74 (2H, m), 1.74–2.30 (2H, m), 2.35–2.50 (2H, m), 2.68 (3H, s), 2.60–3.25 (8H, m), 3.25–3.60 (2H, m), 4.48–4.75 (1H, m), 5.70 (2H, brs), 6.70 (1H, s), 6.88–7.15 (1H, m), 7.16–7.40 (5H, m), 10.15 (1H, s).

Example 43

150 mg of 10% palladium-carbon was added to 11 g of 4-{4-[N-methyl-N-(2-phenylethyl)amino]-1-piperidinyl}carbonyl-2-benzyloxyquinoline (obtained in Reference Example 2) in 20 ml of ethanol. The mixture was stirred at room temperature at a hydrogen pressure of 1 atm. for 1 hour. The reaction mixture was filtered to remove the catalyst. The filtrate was concentrated under reduced pressure. The residue was crystallized from diethyl ether and then re-crystallized from ligroin-ethyl acetate to obtain 0.3 g of 4-{4-[N-methyl-N-(2-phenylethyl)amino]-1-piperidinyl}carbonylcarbostyril as a white powder having a melting point of 155°–158° C.

By using suitable starting materials, the compounds of Examples 1–15 and 17–42 were obtained in the same manner as in Example 43.

Example 44

0.5 g of 5% palladium-carbon was suspended in 0 ml of ethanol. Thereto was added 5 g of 8-nitro-6-{4-[N-methyl-N-(2-phenylethyl)amino]-1-piperidinylcarbonyl}-3,4-dihydrocarbostyril. The mixture was subjected to catalytic reduction at 30°–40° C. at normal pressure in a water bath. After the completion of hydrogen absorption, the reaction mixture was filtered to remove the catalyst. The catalyst was washed with ethanol. The filtrate and the washings were mixed. The mixture was subjected to distillation to remove the solvent to obtain 4.6 g of 8-amino-6-{4-[N-methyl-N-(2-phenylethyl)amino]-1-piperidinylcarbonyl}-3,4-dihydrocarbostyril as a white amorphous.

$^1$H-NMR (200 MHz, CDCl$_3$) δ (ppm): 1.30–1.67 (2H, m), 1.67–2.00 (2H, m), 2.37 (3H, s), 2.53–3.20 (10H, m), 3.83–4.30 (2H, m), 4.45–4.90 (1H, m), 6.65 (2H, brs), 7.13–7.47 (5H, m), 9.75 (1H, brs).

Example 45

In 10 ml of ethanol was dissolved 1 g of 8-amino-6-{4-[N-methyl-N-(2-phenylethyl)amino]-1-piperidinylcarbonyl}-3,4-dihydrocarbostyril. Thereto was added 0.3 g of benzaldehyde. The mixture was refluxed by heating, for 4 hours in an oil bath. The reaction mixture was allowed to cool and then mixed with 0.15 g of sodium boron hydride. The mixture was stirred at room temperature for 4 hours and subjected to distillation under reduced pressure to remove the solvent. The residue was mixed with water. The mixture was extracted with methylene chloride. The extract was dried with anhydrous sodium sulfate and subjected to distillation to remove the solvent. The residue was purified by silica gel column chromatography (elutant: methylene chloride/methanol=100/1~50/1~20/1). The eluate was subjected to distillation to remove the solvent. The residue was recrystallized from ethanol-n-hexane to obtain 0.8 g of 8-benzylamino-6-{4-[N-methyl-N-(2-phenylethyl)amino]-1-piperidinylcarbonyl}-3,4-dihydrocarbostyril as a light yellow powder having a melting point of 144.5°–145.5° C.

Example 46

1.4 g of 6-{4-[N-methyl-N-(2-phenylethyl)amino]-1-piperidinylcarbonyl}carbostyril was gradually added, at room temperature, to a suspension of 170 mg of sodium hydride in 20 ml of dimethylformamide. The mixture was stirred at 50° C. for 1 hour. The reaction mixture was ice-cooled. Thereto was dropwise added 0.27 ml of methyl iodide. The ice bath was removed and the mixture was stirred for 30 minutes. The reaction mixture was poured into ice water. The mixture was extracted with methylene chloride. The extract was washed with water and a saturated aqueous sodium chloride solution in this order, dried with anhydrous magnesium sulfate and concentrated under reduced pressure to remove the solvent. The residue was purified by a silica gel column chromatography (elutant: methylene chloride/methanol=50/1). The resulting material was treated with hydrochloric acid to convert into a hydrochloride. The hydrochloride was dissolved in ethanol. The solution was poured into excessive diethyl ether for solidification to obtain 1.1 g of 1-methyl-6-{4-[N-methyl-N-(2-phenylethyl)amino]-1-piperidinylcarbonyl}carbostyril hydrochloride as a white powder.

$^1$H-NMR (200 MHz, DMSO-d$_6$) δ (ppm): 1.55–1.95 (2H, m), 1.95–2.30 (2H, m), 2.78 (3H, d, J=4.6 Hz), 2.85–3.50 (7H, m), 3.64 (3H, s), 3.50–5.00 (3H, m), 6.68 (1H, d, J=9.6 Hz), 7.20–7.45 (5H, m), 7.58 (1H, d, J=8.8 Hz), 7.68 (1H, dd, J=1.8 Hz, 8.8 Hz), 7.83 (1H, d, J=1.8 Hz), 7.96 (1H, d, J=9.6 Hz), 10.75–10.95 (1H, m).

By using suitable starting materials, the compounds of Examples 22 and 23 were obtained in the same manner as in Example 46.

Example 47

A suspension of 0.75 g of 6-(4-methylamino)-1-piperidinylcarbonyl)-3,4-dihydrocarbostyril hydrochloride and 1.28 g of potassium carbonate in 20 ml of acetonitrile was stirred at room temperature for 30 minutes. Thereto was added 1.0 g of 2-phenylthioethyl bromide. The mixture was refluxed by heating, for 5 hours. After natural cooling, the insoluble portion was collected by filtration and washed with diethyl ether. The filtrate and the washings were mixed. The mixture was concentrated under reduced pressure. The residue was purified by a silica gel column chromatography (elutant: dichloromethane/methanol=50/1 to 25/1). The resulting material was treated with hydrochloric acid to convert into a hydrochloride. The hydrochloride was crystallized from ethanol-diethyl ether to obtain 0.59 g of 6-{4-[N-methyl-N-(2-phenylthioethyl)amino]-1-piPeridinylcarbonyl}-3,4-dihydrocarbostyril hydrochloride as a white powder.

$^1$H-NMR (200 MHz, DMSO-d$_6$) δ (ppm): 1.45–1.85 (2H, m), 1.85–2.20 (2H, m), 2.38–2.58 (2H, m), 2.73 (3H, d, J=4.6 Hz), 2.80–3.08 (4H, m), 3.10–3.70 (5H, m), 3.70–4.70 (2H, m), 6.89 (1H, d, J=8.0 Hz), 7.15–7.50 (7H, m), 10.26 (1H, s), 10.90–11.20 (1H, m).

By using suitable starting materials, the compounds of Examples 1 and 3–42 were obtained in the same manner as in Example 47.

Pharmacological Test

Materials and Method Used in the Test

A preparation for perfusing blood in femoral artery under a constant pressure was prepared as follows.

Adult male or female mongrel dogs each weighing about 15–30 kg were anesthetized with pentobarbital sodium (30 mg/kg i.v.). Heparin sodium (700 U/kg) was administered to them intravenously. Then, the arterial blood of each dog was perfused from the carotid to the right femoral artery using a reciprocating pump at a rate of 90 ml/min. A Starling's air damper was provided in parallel to the perfusion circuit to maintain the perfusion pressure at 100 mmHg. The blood which had passed through the air damper, was returned to the sample from the left femoral vein.

During the test, a tracheal cannula was fitted to practise artificial respiration using an artificial respirator (a product of Shinano Seisakusho), and pentobarbital sodium (4 mg/kg/hr) and heparin sodium (100 U/kg/hr) were continuously administered intravenously to maintain anesthesia and the anti-coagulation activity of blood.

The amount of blood flow in femoral artery was measured in the perfusion circuit by the use of an electromagnetic blood flow meter (MFV-2100 manufactured by Nihon Koden) and reported on a thermal-pen type recorder (RECTI-HORIZ 8K manufactured by Nihon Denki Sanei).

Each of the test compounds shown below was dissolved in a solvent (purified water, hydrochloric acid, N,N-dimethylformamide) in a concentration of 10 µ/ml. The solution was diluted as necessary and a volume of 10–30 µl was administered into the femoral artery of each dog.

In the test results, the amount of blood flow of test compound-administered group minus the amount of blood flow of control group (solvent alone-administered group) was reported as change in blood flow amount (ml/min). The results are shown in Table 15.

Test Compounds 1. 6- {4-[N-methyl-N-(2-phenoxyethyl)amino]-1-piperidinylcarbonyl}-3,4-dihydrocarbostyril
2. 6-{4-[N-methyl-N-(2-phenylethyl)amino]-1-piperidinylcarbonyl}-3,4-dihydrocarbostyril
3. 6-{4-[N-methyl-N-(3-phenylpropyl)amino]-1-piperidinylcarbonyl}-3,4-dihydrocarbostyril
4. 6-{4-[N-ethyl-N-(2-phenoxyethyl)amino]-1-piperidinylcarbonyl}-3,4-dihydrocarbostyril hydrochloride
5. 6-{4-[N-methyl-N-(2-phenylethyl)amino]-1piperidinylcarbonyl}-8-methyl-3,4-dihydrocarbostyril hydrochloride
6. 3-Methyl-6-{4-[N-methyl-N-(2-phenylethyl)amino]-1-piperidinylcarbonyl}carbostyril
7. 8-Methyl-6-{4-[N-methyl-N-(2-phenylethyl)amino]-1-piperidinylcarbonyl}carbostyril
8. 6-{4-[N-methyl-N-(2-phenylethyl)amino]-1-piperidinylcarbonyl}carbostyril
9. 6-[4-{N-methyl-N-[2-(3-methoxyphenoxy)ethyl]amino}-1-piperidinylcarbonyl]-3,4-dihydrocarbostyril
10. 1-Methyl-6-{4-[N-methyl-N-(2-phenylethyl)amino]-1-piperidinylcarbonyl}carbostyril hydrochloride
11. 8-{4-[N-methyl-N-(2-phenylethyl)amino]-1-piperidinylcarbonyl}-3,4-dihydrocarbostyril hydrochloride
12. 5-{4-[N-methyl-N-(2-phenylethyl)amino]-1-piperidinylcarbonyl}carbostyril hydrochloride
13. 4-{4-[N-methyl-N-(2-phenylethyl)amino]-1-piperidinylcarbonyl}-3,4-dihydrocarbostyril hydrochloride
14. 8-Ethyl-6-{4-[N-methyl-N-(2-phenylethyl)amino]-1-piperidinylcarbonyl}-3,4-dihydrocarbostyril oxalate
15. 8-Ethyl-6-{4-[N-methyl-N-(2-phenylethyl)amino]-1-piperidinylcarbonyl}carbostyril hydrochloride
16. 8-Nitro-6-{4-[N-methyl-N-(2-phenylethyl)amino]-1-piperidinylcarbonyl}carbostyril hydrochloride
17. 4-Methyl-6-{4-[N-methyl-N-(2-phenylethyl)amino]-1-piperidinylcarbonyl}carbostyril hydrochloride
18. 1-Methyl-8-ethyl-6-{4-[N-methyl-N-(2-phenylethyl)amino]-1-piperidinylcarbonyl}-3,4-dihydrocarbostyril oxalate
19. 8-Methoxy-5-{4-[N-methyl-N-(2-phenylethyl)amino]-1-piperidinylcarbonyl}-3,4-dihydrocarbostyril dihydrochloride
20. 8-Methoxy-5-{4-[N-methyl-N-(2-phenylethyl)amino]-1-piperidinylcarbonyl}carbostyril dihydrochloride
21. 8-Amino-6-{4-[N-methyl-N-(2-phenylethyl)amino]-1-piperidinylcarbonyl}-3,4-dihydrocarbostyril
22. 8-propyl-6-{4-[N-methyl-N-(2-phenylethyl)amino]-1-piperidinylcarbonyl}carbostyril hydrochloride
23. 7-Methoxy-6-{4-[N-methyl-N-(2-phenylethyl)amino]-1-piperidinylcarbonyl}-3,4-dihydrocarbostyril hydrochloride
24. 7-Methyl-6-{4-[N-methyl-N-(2-phenylethyl)amino]-1-piperidinylcarbonyl}-3,4-dihydrocarbostyril oxalate
25. 7-Methoxy-6-{4-[N-methyl-N-(2-phenylethyl)amino]-1-piperidinylcarbonyl}carbostyril
26. 8-Methoxy-6-{4-[N-methyl-N-(2-phenylethyl)amino]-1-piperidinylcarbonyl}carbostyril hydrochloride
27. 8-Methoxy-6-{4-[N-methyl-N-(2-phenylethyl)amino]-1-piperidinylcarbonyl}-3,4-dihydrocarbostyril hydrochloride

TABLE 15

| Test compound No. | Dose (nM) | Change in blood flow amount (ml/min) | Test Compound No. | Dose (nM) | Change in blood flow amount (ml/min) |
| --- | --- | --- | --- | --- | --- |
| 1 | 30 | 10.0 | 15 | 100 | 13.3 |
| 2 | 30 | 13.7 | 16 | 100 | 16.0 |
| 3 | 30 | 14.0 | 17 | 100 | 13.0 |
| 4 | 100 | 12.5 | 18 | 100 | 7.0 |
| 5 | 100 | 10.3 | 19 | 100 | 19.3 |
| 6 | 100 | 8.3 | 20 | 100 | 13.5 |
| 7 | 100 | 11.5 | 21 | 100 | 7.3 |
| 8 | 100 | 11.5 | 22 | 100 | 13.8 |
| 9 | 100 | 7.0 | 23 | 100 | 12.0 |
| 10 | 100 | 11.0 | 24 | 100 | 10.0 |
| 11 | 100 | 10.3 | 25 | 100 | 14.0 |
| 12 | 100 | 10.5 | 26 | 100 | 19.0 |
| 13 | 100 | 10.5 | 27 | 100 | 15.5 |
| 14 | 100 | 10.3 | | | |

We claim:

1. A carbostyril compound of the general formula (1A):

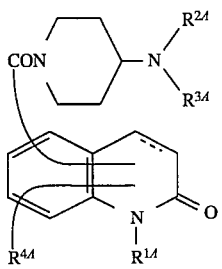 (1A)

wherein, $R^{1A}$ is a hydrogen atom or a lower alkyl group; and $R^{3A}$ are each the same or different, and are each a hydrogen atom, a lower alkyl group, a phenylthio-lower alkyl group, a phenoxy-lower alkyl group having 1 to 3 substituents, in the phenyl ring, selected from the group consisting of a halogen atom and a lower alkoxy group or a phenyl-lower alkyl group; $R^{4A}$ is a hydrogen atom, a lower alkyl group, a lower alkoxy group, a nitro group, an amino group, or a phenyl-lower alkylamino group; and the carbon-carbon bond between the 3- and 4-positions in the carbostyril skeleton is a single bond or a double bond or a salt thereof; provided that when $R^{1A}$ and $R^{4A}$ are hydrogen atoms at the same time, the substituent of the formula:

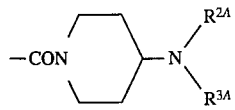

is substituted at the 6-position in the carbostyril skeleton, and one of $R^{2A}$ and $R^{3A}$ is a hydrogen atom, a lower alkyl group or a phenyl-lower alkyl group, then the other of $R^{2A}$ and $R^{3A}$ should not be a hydrogen atom, a lower alkyl group or a phenyl-lower alkyl group.

2. The carbostyril compound or salt thereof according to claim 1, wherein $R^{1A}$ is a hydrogen atom; and $R^{4A}$ is a lower alkyl group, a lower alkoxy group or a nitro group.

3. The carbostyril compound or salt thereof according to claim 1, wherein $R^{1A}$ is a hydrogen atom; and $R^{4A}$ is an amino group or a phenyl-lower alkylamino group.

4. The carbostyril compound or salt thereof according to claim 1, wherein $R^{1A}$ is a lower alkyl group.

5. The carbostyril compound or salt thereof according to claim 1, wherein $R^{4A}$ is a hydrogen atom.

6. The carbostyril compound or salt thereof according to claim 1, wherein $R^{2A}$ is a lower alkyl group.

7. The carbostyril compound or salt thereof according to claim 1, wherein $R^{2A}$ is a phenyl-lower alkyl group.

8. The carbostyril compound or salt thereof according to claim 1, wherein $R^{2A}$ is a phenylthio-lower alkyl group or a phenoxy-lower alkyl group having 1 to 3 substituents, in the phenyl ring, selected from the group consisting of a halogen atom and a lower alkoxy group.

9. The carbostyril compound or salt thereof according to claim 1, wherein $R^{2A}$ is a lower alkyl group; $R^{3A}$ is a phenyl-lower alkyl group; $R^{1A}$ is a hydrogen atom; and $R^{4A}$ is a lower alkyl group, a lower alkoxy group or a nitro group.

10. The carbostyril compound or salt thereof according to claim 1, wherein $R^{2A}$ is a hydrogen atom or a lower alkyl group; and $R^{3A}$ is a phenylthio-lower alkyl group, a phenoxy-lower alkyl group having 1 to 3 substituents, in the phenyl ring, selected from the group consisting of a halogen atom and a lower alkoxy group, or a phenyl-loweralkyl group.

11. The carbostyril compound or salt thereof according to claim 6, wherein $R^{1A}$ is a hydrogen atom; and $R^{4A}$ is a lower alkyl group, a lower alkoxy group or a nitro group.

12. The carbostyril compound or salt thereof according to claim 6, wherein $R^{1A}$ is a hydrogen atom; and $R^{4A}$ is an amino group or a phenyl-lower alkylamino group.

13. The carbostyril compound or salt thereof according to claim 6, wherein $R^{1A}$ is a lower alkyl group.

14. The carbostyril compound or salt thereof according to claim 7, wherein $R^{1A}$ is a hydrogen atom; and $R^{4A}$ is a lower alkyl group, a lower alkoxy group or a nitro group.

15. The carbostyril compound or salt thereof according to claim 7, wherein $R^{1A}$ is a hydrogen atom; and $R^{4A}$ is a phenyl-lower alkylamino group.

16. The carbostyril compound or salt thereof according to claim 7, wherein $R^{1A}$ is a lower alkyl group.

17. The carbostyril compound or salt thereof according to claim 8, wherein $R^{1A}$ is a hydrogen atom; and $R^{4A}$ is a lower alkyl group, a lower alkoxy group or a nitro group.

18. The carbostyril compound or salt thereof according to claim 8, wherein $R^{1A}$ is a hydrogen atom; and $R^{4A}$ is an amino group or a phenyl-lower alkylamino group.

19. The carbostyril compound or salt thereof according to claim 8, wherein $R^{1A}$ is a lower alkyl group.

20. The carbostyril compound or salt thereof according to claim 8, wherein $R^{4A}$ is a hydrogen atom.

21. The carbostyril compound or salt thereof according to claim 10, wherein $R^{1A}$ is a hydrogen atom; and $R^{4A}$ is a lower alkyl group, a lower alkoxy group or a nitro group.

22. The carbostyril compound or salt thereof according to claim 10, wherein $R^{1A}$ is a hydrogen atom; and $R^{4A}$ is an amino group or a phenyl-lower alkylamino group.

23. The carbostyril compound or salt thereof according to claim 10, wherein $R^{1A}$ is a lower alkyl group.

24. The carbostyril compound or salt thereof according to claim 10, wherein $R^{4A}$ is a hydrogen atom.

25. The carbostyril compound or salt thereof according to claims 9, 21, 22, 23 or 24, wherein the side-chain of the formula:

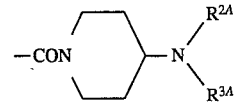

is substituted at 5- or 6-position in the carbostyril skeleton; and $R^{4A}$ is substituted at 7- or 8-position in the carbostyril skeleton.

26.  6-{4-[N-Methyl-N-(2-phenylethyl)amino]-1-piperidinyl}carbonyl-8-ethylcarbostyril.

27.  6-{4-[N-Methyl-N-(2-phenylethyl)amino]-1-piperidinyl}carbonyl-8-methylcarbostyril.

28.  5-{4-[N-Methyl-N-(2-phenylethyl)amino]-1-piperidinyl}carbonyl-8-methoxycarbostyril.

29.  6-{4-[N-Methyl-N-(2-phenylethyl)amino]-1-piperidinyl}carbonyl-8-methoxycarbostyril.

30. A pharmaceutical composition having peripheral vasodilating activity comprising, as the active ingredient, a carbostyril compound or a pharmaceutically acceptable salt thereof of claim 1 and a pharmaceutically acceptable carrier.

31. A method for treating a patient in need of peripheral vasodilating activity comprising administering to such patient an effective amount of a pharmaceutical composition comprising, as the active ingredient, a carbostyril compound or pharmaceutically acceptable salt thereof of the general formula (1):

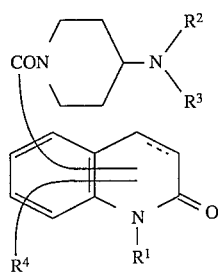

wherein $R^1$ is a hydrogen atom or a lower alkyl group; $R^2$ and $R^3$ are the same or different, and are each a hydrogen atom, a lower alkyl group, a phenylthio-lower alkyl group, a phenoxy-lower alkyl group which may have 1 to 3 substituents, in the phenyl ring, selected from the group consisting of a halogen atom and a lower alkoxy group, or a phenyl lower alkyl group; $R^4$ is a hydrogen atom, a lower alkyl group, a lower alkoxy group, a nitro group, an amino group, or a phenyl-lower alkylamino group; and the carbon-carbon bond between the 3- and 4-positions in the carbostyril skeleton is a single bond or a double bond and a pharmaceutically acceptable carrier.

* * * * *

UNITED STATES PATENT AND TRADEMARK OFFICE
CERTIFICATE OF CORRECTION

PATENT NO. : 5,591,751
DATED : January 7, 1997
INVENTOR(S) : Takafumi Fujioka et al.

It is certified that error appears in the above-indentified patent and that said Letters Patent is hereby corrected as shown below:

Claim 1, column 53, line 12, insert --$R^{2A}$-- before "and".

Signed and Sealed this

Twenty-ninth Day of April, 1997

*Attest:*

BRUCE LEHMAN

*Attesting Officer*     *Commissioner of Patents and Trademarks*